United States Patent
Wang et al.

(10) Patent No.: US 8,426,574 B2
(45) Date of Patent: Apr. 23, 2013

(54) IDENTIFICATION OF ASTROVIRUS VA1 ASSOCIATED WITH GASTROENTERITIS IN HUMANS

(75) Inventors: David Wang, St. Louis, MO (US); Herbert Whiting Virgin, IV, St. Louis, MO (US); Guoyan Zhao, St. Louis, MO (US); Stacy Finkbeiner, St. Louis, MO (US); Jan Vinje, Decatur, GA (US); Yan Li, Tucker, GA (US); Suxiang Tong, Duluth, GA (US)

(73) Assignees: Washington University, St. Louis, MO (US); The United States of America, as Represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 222 days.

(21) Appl. No.: 12/790,618

(22) Filed: May 28, 2010

(65) Prior Publication Data
US 2011/0008353 A1 Jan. 13, 2011

Related U.S. Application Data

(60) Provisional application No. 61/182,008, filed on May 28, 2009.

(51) Int. Cl.
*C07H 21/00* (2006.01)
*C12Q 1/70* (2006.01)
*A61K 39/12* (2006.01)

(52) U.S. Cl.
USPC .................. 536/23.72; 435/5; 424/204.1

(58) Field of Classification Search .................. None
See application file for complete search history.

(56) References Cited

PUBLICATIONS

Finkbeiner et al., Virol. J. (2008) 5:117.
Finkbeiner et al., PLoS Pathog. (2008) 4:e1000011.
Holtz et al., Virol. J. (2008) 5:159.
Mendez et al., Fields Virology, 5$^{th}$ ed., (2007) Knipe and Howley, (eds.) Philadelphia: Lippincott Williams & Wilkins, pp. 981-1000.

*Primary Examiner* — Stacy B. Chen
(74) *Attorney, Agent, or Firm* — Morrison & Foerster LLP

(57) ABSTRACT

Provided herein is a novel human astrovirus, its nucleic acid sequence, as well as methods to detect and diagnose the presence of the astrovirus.

6 Claims, 6 Drawing Sheets

SEQ ID NO: 1
```
CCAAATTTGTTGGCTGTGCCGATTGGCACTGGTGGGTCATGGAGCGCTCATACAAGCCTAGTGGCAGTAGCCACTATGA
TCCCTATGATAGGGTACTACAACATGGCAGTGTCAAAGCACGGATACAGGGCCTTCAGCTTAATAAAGTAGCTAAAACC
AAGCTTGAAGAGATTTTTTCATGTGGTGGGCCCTTGTGTTTTGGCTATGGTGATGTTGAGACTACTCGTGTCTCAAATG
GAGTTGTTGAGCCACAACCTTTAATTGTTAAGACGGTCTATGTCTCAGGAGTGAGAGAGGGTAATGAATATGTCACTTA
CCTTTTTAAACCGGGACTTAATGATTGGGTTGAGGTTGATGCTAACATACATAAACCTACTGCCATTGTTGGTGTATTG
TATCATGAGTATAACAGGCTTAAATTAGAGAATGAAAGTTTGAAAACAGAGCGCTCATCTTTACAATTGGATATATCAA
TCCTCAGACATGAGCTTGAGCGTGCAAGACCACCAACTAAAATAATTAGGCCTTTCAGTGTTGGGTGCATTATACTGTA
TGGTTTACTGATTGGCCTTTTGTTTTCACACATCTCACAAGCTTTTAGGACTGGTGTGTGTCTTGATCCAGATGTTGGT
GAAACACTAAAGCCACAAACCTGTATAAACTGGAAGTGGGATGGTGGAATTGAATCAGATGAGACTATTCCATTTTATG
ATAGGTTTACAGCTTGGTATACAGGTTTAATACAACAGTTTAAAAGTATGTACAATGACATTGTCATTGATTTAGTGGT
CCAGGCTTTTGGCTTTGCTTACACATGGACAGCTATAGCACTGATGATAGGCACATATTATATGTTGAAATCCACCAGC
CCAGCATATATGCTGGTGACATTGATGATGGCAACTGTGTCAAGAATGCAGTTATTTGCAATATCTGCTATACCTAATA
TGGAGGTCACTTCAATGTTTTCATTGTGGTGCTGTATGGTATTATACTATTTTAATCAGGTTGCAGCAATGGCTGCGTC
ATTAATGATAGCAGCTATGTGCTCTATTGTTTGCCTTTTCATGGGTGATGCTGAGTATGTGAAAGTGATAAGGGGCCAT
GGCGTGGTTATCTTAACTGTTGTTGTTTCCCACATCTTTAGTGTCTTGTTAGTGCCACACTGGGTCACAGTGTTCCTAA
TAGTTGCTTTTAGAATTGTTAGGTTAATTGGAGCAGTTGTTGGTGAGAAAATAGAAGTTAGAAATTCTGAGGGAAAAGT
TACAAGTGTCATACCAACAACAACGTCCTGGTTAAATCGGATTTCTGGATTTGTTCAGTCCAAATTTACCCAAAAAGTT
AGAACTGGTATAATGTCAACAGCTAGAGTGATACCTAATGGTGTTGTCATTGTCGAATCAAAAGAAAGCTCAGGTACTG
GCTTCAGGGTTCAAAATTACATAGTCACAGCCGGGCATGTTGTTGGCAATGAAACACAAATAAAGGTTAAGTGGGGAGA
TGTTAATGTTTACACAAAAGTTGTTTACATGCATCCCACTAAGGATATAGCCTATCTTGCCTTACCATCAGAGTATCAA
GCACTCCCAACATACAAGTTTGCTAAGCTGATTGAGGATGGCACCGTTGTCATAACATCAATGGAGGACTGTGGTGTCC
TTGCCGTTGCGGTTACAGAAGGTGTTATTGTTAAAGATAACATAACATAGCTGTTAGCACCCGAAACGGCATGAGTGG
TTCACCTGTTACAAATGTTGATGGTAGAATTGTTGGCATACATCAAGCCAACACTGGATTTACAGGCGGTGCTGTCATT
ATAAAGCAAGAGGATTTACCACCCCAAAAGAAGCCACAAAGGGAGATAGACCTTGAGAACAAAATTAAAGAATTAGAGG
ATGCCCTTAAAGGTCAGATGAATCAAGGCCTAAATGAAAATCAGATAGTCGAATTGATTCGGCTTGCTGTTGGTCGTGA
GATCGAAATCTTACGGCATGAAATCAATATGAACCAAGCAAAAGGTAAAAATAAAAGGAAGAATCACCACAAGAGGCGC
AGGAAGGGAAAAGTTTGGACTGAAGAGGAGTACAAAGACCTTTTGGAAAAGGGATTTACCAGACAGCAATTACGGGACA
TGGCTGAAGTGCTAAGAGAGGCAGATTATTCTGAAGATGATGAAAGTGATGAGTATGACACTGGTTATCCGCAATGGTC
AGACCCAGAAGACTCTGAGGAGGTTGAAAGGGAATGGTTTGGGCCAAAGAAAAAGATACTTGATGAGGTTGAAGAAGGT
TGGTCCAATACTGATTTCTGGGAGCAGTGTCAGAAGGTGTGGAAGGAGATGGAGCCCATGCCGGAAGAATCTGTTAACA
CTTTACCGTCACACTTGAGTGATAAGTATGGTATTACATGCTATGTTGTCACAAAGAGTGATATGGAAGCCTTAGCCCG
TGATTTGCAGGAATACCAAGCCAAGGTTGAGGAGAAGATTAAGGCAAATGTTGTTCGTGGTCAGTGGCTTGAGGGAGTC
AATCCAAAAACTATCATAAGTGAGTTGGATGAATTATGGCTGAAACTGAACCACTTAATGTGGACCCATGGTATAGTCC
CTTTCACACAGAGGAAAAAAATTAACAGAAGAAAACAGCAAAAAAACTTGAAGGGGGCCCCGAAACAGGGGCCCAAAA
CCAGAACAACTAAGGCTTGGGTACTGGAGAGAACTATTAAAACCTGGTGAATATTATCTTACCCCCCCACATTGCCCCT
TAGTTGGTGTTTTACCAATAGATAGGCCTATAAGTGATTATGATGAGCCAATTGATGATTTACTAAATTTGTTGCCAAA
ATGTGAGGAAAAGCCGCCATACGCACCGTCTACATGGGACCAGAAGCGTATAGGCGGTCATTTGATAAGTTCTTTTAC
AGAAAGCCAACTGAAAATATAAGAGAAAAATATCCTAGGGAGTGGAAATTTGCAATGTCAGTGCTCAGAAGAGAATTTG
ATTTCCTACAGGACAGTGTTCTTATTGACATAACATCCACTTCAAAGAATGCTGACTCCACACCTGCTTATCCAAAGAC
ATTATGGTGGAAAACTGAAACAGAATACCTTAAAGAGCGGGGTTACCAAGATTACATTAAAGAGTTAGATTCAATAAGA
TCTGGAGAGAGGCCTGATGTCTTATGGTATTTATTTTAAAAAAAGAGATTTTAAAGATAAGTAAAATTGAGGAAGAAG
ACATTAGGCAAATTGTTTGTGCTGATCCCATTTTTTCTAGAATTGGTTGTGTATTTGAAGAGCACCAAAATCAATTGAT
GAAAAATCGAACCCTGACACGTATGGGTCAATGTGGATGGTCACCATTTATGGGAGGTTTCCATAAACGCATAAAGCGC
CTAGTTGATAAAGGCAATGATTACTTCATTGAGTTCGACTGGACGCGTTATGATGGTACCATCCCTAATGAAGTCTTTA
AGGCTATTAAGGACTTTAGATTCTCGTGTCTTAGGGGAGACTTGCAAACAAAAGAAAACAGAGATGTCTATAATTGGTA
TTGTGAGAACATATTTAGAAGATATGTGATGTTACCTTCAGGAGAAGTGACAATCCAGGACAGGGGGAACCCCTCTGGA
CAAATATCCACAACTATGGATAATAACATCTGTAATGTCTTTTTCCAGGCATTTGAGTTTGCATATCTGAATACTGAAT
TGGATTCTGATGAATTGAAGGAAAATTGGGATAAGTATGACTCACTTATCTATGGAGATGACAGGCTAACCACAACCCC
TATTTTATGTGACAATTATGTGGACAGAGTTATTAAAATGTATGCTGATGTCTTGGGATGTGGGTCAAGAGAGAGAAA
GTAAAAGTTTCAAATGAAATTAATGGATTGACCTTTTGTGGCTTTACTGTTCAAGAGTCAAATGGCCTTTTGTCCCCA
TACCAACTGATACAGATAAATTACTTGCTGGCTTAATAACACCAATAAAGAATTGCCTGATATTTTGTCACTCTATGG
GAAGCTCCTTTGCTACCGCATCCTTGGCCATAACTTGCCTGATGACCATAAATTTAAAAATTATATCTTGGTCGCCTTG
GAGGTAGTGGCCAGGCACATCCGTGCTAGTGGTGGGAAGAACCCTATTATATCACGGATAGCATGCTGGATAGGCTTT
GGAGGGGAGGTCCAAAGCAAAGTCATGGCTGGTAGGCAGCCCCAGCAGGCCCTGCCCAAGGCAGCGGCAAAGCAAATAG
CCAAGGAGGTAGTCAAACAGGAGAAGAAGGAACCAGTGGTGCGTAAAAAGAAACAGTTTTATCCAAATCCAAAGTTTAA
TAATAGATTTAATAAGAAATTTGTGAAAAAACAGCTAGATAAAAATTTGAAGAAACAAGGGTTTGAAGGACCAAAACCT
AGATTTGCTGTCACCGTCTCTGCCACCATTGGCAAGGTCGGGCCAAATAAAAGTCAGGGACCTGAACTCCAAATATCCA
```

```
CTTTCATGCATCCCAGCTTGATGAAAGAGCCAAATGATGGCACAAATTTTGGTCCCCTACAGTCAGCAGCTGCACAATG
GGGTTTGTGGCGCTTGAAAAATTTGAGCGTCACGTTTACTCCCCTTGTTGGTCCATCAGCAGTTACCGGGTCTGTTTTC
CGCATATCCCTAAACATGGCACAGTCACCTGGAGCCACGTCATGGGGGGGTCTTGGTGCTAGGAAGCACAAGGATGTTG
CTGTGGGAAAGCAGTTCACTTGGAAGCTACAGAAGGGAGACCTCACAGGCCCCAGGGAAACCTGGTGGCTTACAGACAC
AAATGAAGAGGGAGCACAAAGTTGTGGGCCTCTTCTTGAGATCCATGGCCTTGGTGAAACAACTTCTACATACAAGGAT
GCAGCATGGGCTGGAGACCTCTTCATTGTTGAGGTCAGGGGTCGCTGGGAGTTTGCAAATTACAACAGCAAACCTGCAT
TAGGCATGTTGGAGAGGGTGACTGAAACTACCAATGCTTCAATTGAAGTAGCTAATGGCAATATGATTATGACAGTTCC
ACAGAATTCCCAGCTTGCAAGGCATATGAGTGAAAGGTTCGAGAGGACCACAAATGCAAGTACTGTTGGTGAAACAATA
TGGCAGATTGTGGATGAGGGTGCTGGTTTGGTTGCAAATGTCGCACCACCCCCGTTCACTTGGTTGATCAAAGGGGGAT
GGTGGTTTGTCAAGAAATTACTAGGTAGATCAGCAAATACTGATGTCCAATATCTAGTTTATGCATCATTGGCAGACGC
CCAAAACAATAGACCTGTAGAGGCACAAAATTACACAAAAGTCACACGACAGACAACACTTTCTTCCACGCAAATCAAT
GCACCTAACACAGGCCCTAACACCACTACAGGGTCAATTGGAAATAACAACCAACAGTGGCCGATACCTCCGACAGGGG
TGCCGGTTGGTGACTTTTATGTCTGTGGCAGGATGACAACATTGCATATGGGTGGTCAGTCTGGCATTCAAGCCACGAC
TCTAGTGAATGGGATGATATATCGTACAGACCACCCAGAACCATCAACAAGCCCAGTTTCCAATTGGGAATTCACAGTT
TTGGAAAACAACACAATTGTTGGTGCTGGAATGGGGTGTGTGTGGTTTCAGAAATCCGAAGCACTAGTGTGGACGCTAG
ATGGCCAGAAGCTGTCAGGATGGAACACACTAGATGGTGTTGGTACAACCCAATTGACAGTCGCCTGGAGACAGCATAA
CAGAACAATTTATGGATGGGCTAATGTTGTTGCTTGGAACTCTGAAGAATGGCATACAAATGCAGAACAACCACACCAG
CCTATATTGAGGCTGACATATTGGCTAGTAAAAATTAATGTTTTGTCTGAACCAGAAGATTTTGATGTTGTCCAAAAAT
CCCCATTAGCTTATTTAGAAGATTATACTACAGCACAATCAAAATCTGCCATCCAAAAGCTCAACTTCCAAACGTTTCA
GAAACCTGAAGGGGGAGGCACTTTGCGGGCACAATACTCAACTACTCCCAGGCAAGGGGATTTTGCCGTAATATGGCAG
ATTGGTAGACATAATTTTGACATGTCTACCGGTAAGGGTACACCAGTTGAAAGTTTGAGTGATTATGTCATGCCCCAGC
AGAAAGATGCCCATATTGGTATGTGGTATCGTGCTTTAACCAGTGTTGGACCAAGATCAGATGTTTTGACCCTTCATTT
CCACTTGCCAACTGTGGAAAAAGATTTGGTTGAGCAGATCATTGATCAAATTCAGCATCGCTACAGATTGACCCCACTG
GATTCGGATTCAGACTCCTCTAGTTCTGATTCCGATTTCGAGCCTGAAGATAGATTTGAGAAGTTAAAAATCTATGAGG
GTCTCAGGTCCAGTGGTCTGTCACACCATGTATCTGATGGTGCTGCGATAGCTGTCAAGAAAAAATTGCGCCGAGGCCA
CGCCGAGTAGGATCGAGGGTACAGCGCTAAATTGATTACTAGAGGTGTTAATCAATAAATCATTGATTTGGTGATTGAT
ATGATCAATTTGAAATTGAAATTTCCAGCAAAAAAAAAAAAAAAAAAAAAAAAAA
```

Figure 2 (page 2 of 2)

SEQ ID NO: 2 (ORF1a)

```
ATGGAGCGCTCATACAAGCCTAGTGGCAGTAGCCACTATGATCCCTATGATAGGGTACTACAACATGGCAGTGTCAAAG
CACGGATACAGGGCCTTCAGCTTAATAAAGTAGCTAAAACCAAGCTTGAAGAGATTTTTTCATGTGGTGGGCCCTTGTG
TTTTGGCTATGGTGATGTTGAGACTACTCGTGTCTCAAATGGAGTTGTTGAGCCACAACCTTTAATTGTTAAGACGGTC
TATGTCTCAGGAGTGAGAGAGGGTAATGAATATGTCACTTACCTTTTTAAACCGGGACTTAATGATTGGGTTGAGGTTG
ATGCTAACATACATAAACCTACTGCCATTGTTGGTGTATTGTATCATGAGTATAACAGGCTTAAATTAGAGAATGAAAG
TTTGAAAACAGAGCGCTCATCTTTACAATTGGATATATCAATCCTCAGACATGAGCTTGAGCGTGCAAGACCACCAACT
AAAATAATTAGGCCTTTCAGTGTTGGGTGCATTATACTGTATGGTTTACTGATGGCCTTTGTTTTCACACATCTCAC
AAGCTTTTAGGACTGGTGTGTGTCTTGATCCAGATGTTGGTGAAACACTAAAGCCACAAACCTGTATAAACTGGAAGTG
GGATGGTGGAATTGAATCAGATGAGACTATTCCATTTATGATAGGTTTACAGCTTGGTATACAGGTTAATACAACAG
TTTAAAAGTATGTACAATGACATTGTCATTGATTTAGTGGTCCAGGCTTTTGGCTTTGCTTACACATGGACAGCTATAG
CACTGATGATAGGCACATATTATATGTTGAAATCCACCAGCCCAGCATATATGCTGGTGACATTGATGATGGCAACTGT
GTCAAGAATGCAGTTATTTGCAATATCTGCTATACCTAATATGGAGGTCACTTCAATGTTTCATTGTGGTGCTGTATG
GTATTATACTATTTTAATCAGGTTGCAGCAATGGCTGCGTCATTAATGATAGCAGCTATGTGCTCTATTGTTTGCCTTT
TCATGGGTGATGCTGAGTATGTGAAAGTGATAAGGGGCCATGGCGTGGTTATCTTAACTGTTGTTGTTTCCCACATCTT
TAGTGTCTTGTTAGTGCCACACTGGGTCACAGTGTTCCTAATAGTTGCTTTTAGAATTGTTAGGTTAATTGGAGCAGTT
GTTGGTGAGAAAATAGAAGTTAGAAATTCTGAGGGAAAAGTTACAAGTGTCATACCAACAACAACGTCCTGGTTAAATC
GGATTTCTGGATTTGTTCAGTCCAAATTTACCCAAAAAGTTAGAACTGGTATAATGTCAACAGCTAGAGTGATACCTAA
TGGTGTTGTCATTGTCGAATCAAAAGAAAGCTCAGGTACTGGCTTCAGGGTTCAAAATTACATAGTCACAGCCGGGCAT
GTTGTTGGCAATGAAACACAAATAAAGGTTAAGTGGGGAGATGTTAATGTTTACACAAAAGTTGTTTACATGCATCCCA
CTAAGGATATAGCCTATCTTGCCTTACCATCAGAGTATCAAGCACTCCCAACATACAAGTTTGCTAAGCTGATTGAGGA
TGGCACCGTTGTCATAACATCAATGGAGGACTGTGGTGTCCTTGCCGTTGCGGTACAGAAGGTGTTATTGTAAAGAT
AACATAACATATGCTGTTAGCACCCGAACGGTCATGAGTGGTTCACCTGTTACAAATGTTGATGGTAGAATTGTTGGCA
TACATCAAGCCAACACTGGATTTACAGGCGGTGCTGTCATTATAAAGCAAGAGGATTTACCACCCCAAAAGAAGCCACA
AAGGGAGATAGACCTTGAGAACAAAATTAAAGAATTAGAGGATGCCCTTAAAGGTCAGATGAATCAAGGCCTAAATGAA
AATCAGATAGTCGAATTGATTCGGCTTGCTGTTGGTCGTGAGATCGAAATCTTACGGCATGAAATCAATATGAACCAAG
CAAAAGGTAAAAATAAAAGGAAGAATCACCACAAGAGGCGCAGGAAGGGAAAAGTTTGGACTGAAGAGGAGTACAAAGA
CCTTTTGGAAAAGGGATTTACCAGACAGCAATTACGGGACATGGCTGAAGTGCTAAGAGAGGCAGATTATTCTGAAGAT
GATGAAAGTGATGAGTATGACACTGGTTATCCGCAATGGTCAGACCCAGAAGACTCTGAGGAGGTTGAAAGGGAATGGT
TTGGGCCAAAGAAAAAGATACTTGATGAGGTTGAAGAAGGTTGGTCCAATACTGATTTCTGGGAGCAGTGTCAGAAGGT
GTGGAAGGAGATGGAGCCCATGCCGGAAGAATCTGTTAACACTTTACCGTCACACTTGAGTGATAAGTATGGTATTACA
TGCTATGTTGTCACAAAGAGTGATATGGAAGCCTTAGCCCGTGATTTGCAGGAATACCAAGCCAAGGTTGAGGAGAAGA
TTAAGGCAAATGTTGTTCGTGGTCAGTGGCTTGAGGGAGTCAATCCAAAAACTATCATAAGTGAGTTGGATGAATTATG
GCTGAAACTGAACCACTTAATGTGGACCCATGGTATAGTCCCTTTCATACAGAGGAAAAAAATTAACAGAAAGAAACAG
CAAAAAAACTTGAAGGGGGCCCCGAAACAGGGGCCCCAAAACCAGAACAACTAA
```

Figure 3

SEQ ID NO: 3 (ORF1a)

```
MERSYKPSGSSHYDPYDRVLQHGSVKARIQGLQLNKVAKTKLEEIFSCGGPLCFGYGDVETTRVSNGVVEPQPLIVKTV
YVSGVREGNEYVTYLFKPGLNDWVEVDANIHKPTAIVGVLYHEYNRLKLENESLKTERSSLQLDISILRHELERARPPT
KIIRPFSVGCILLYGLLIGLLFSHISQAFRTGVCLDPDVGETLKPQTCINWKWDGGIESDETIPFYDRFTAWYTGLIQQ
FKSMYNDIVIDLVVQAFGFAYTWTAIALMIGTYYMLKSTSPAYMLVTLMMATVSRMQLFAISAIPNMEVTSMFSLWCCM
VLYYFNQVAAMAASLMIAAMCSIVCLFMGDAEYVKVIRGHGVVILTVVSHIFSVLLVPHWVTVFLIVAFRIVRLIGAV
VGEKIEVRNSEGKVTSVIPTTTSWLNRISGFVQSKFTQKVRTGIMSTARVIPNGVVIVESKESSGTGFRVQNYIVTAGH
VVGNETQIKVKWGDVNVYTKVVYMHPTKDIAYLALPSEYQALPTYKFAKLIEDGTVVITSMEDCGVLAVAVTEGIVKD
NITYAVSTRNGMSGSPVTNVDGRIVGIHQANTGFTGGAVIIKQEDLPPQKKPQREIDLENKIKELEDALKGQMNQGLNE
NQIVELIRLAVGREIEILRHEINMNQAKGKNKRKNHHKRRRKGKVWTEEEYKDLLEKGFTRQQLRDMAEVLREADYSED
DESDEYDTGYPQWSDPEDSEEVEREWFGPKKKILDEVEEGWSNTDFWEQCQKVWKEMEPMPEESVNTLPSHLSDKYGIT
CYVVTKSDMEALARDLQEYQAKVEEKIKANVVRGQWLEGVNPKTIISELDELWLKLNHLMWTHGIVPFIQRKKINRKKQ
QKNLKGAPKQGPQNQNN
```

Figure 4

SEQ ID NO: 4 (ORF1b)

```
AAAAAACTTGAAGGGGGCCCCGAAACAGGGGCCCCAAAACCAGAACAACTAAGGCTTGGGTACTGGAGAGAACTATTAA
AACCTGGTGAATATTATCTTACCCCCCCACATTGCCCCTTAGTTGGTGTTTACCAATAGATAGGCCTATAAGTGATTA
TGATGAGCCAATTGATGATTTACTAAATTTGTTGCCAAAATGTGAGGAAAAGCCGCCATACGCACCGTCTACATGGGA
CCAGAAGCGTATAGGCGGTCATTTGATAAGTTCTTTTACAGAAAGCCAACTGAAAATATAAGAGAAAAATATCCTAGGG
AGTGGAAATTTGCAATGTCAGTGCTCAGAAGAGAATTTGATTTCCTACAGGACAGTGTTCTTATTGACATAACATCCAC
TTCAAAGAATGCTGACTCCACACCTGCTTATCAAAGACATTATGGTGGAAAACTGAAACAGAATACCTTAAAGAGCGG
GGTTACCAAGATTACATTAAAGAGTTAGATTCAATAAGATCTGGAGAGAGGCCTGATGTCTTATGGTATTTATTTTAA
AAAAAGAGATTTTAAAGATAAGTAAAATTGAGGAAGAAGACATTAGGCAAATTGTTTGTGCTGATCCCATTTTTCTAG
AATGGTTGTGTATTTGAAGAGCACCAAAATCAATTGATGAAAAATCGAACCCTGACACGTATGGGTCAATGTGGATGG
TCACCATTTATGGGAGGTTTCCATAAACGCATAAAGCGCCTAGTTGATAAAGGCAATGATTACTTCATTGAGTTCGACT
GGACGCGTTATGATGGTACCATCCCTAATGAAGTCTTTAAGGCTATTAAGGACTTTAGATTCTCGTGTCTTAGGGGAGA
CTTGCAAACAAAAGAAAACAGAGATGTCTATAATTGGTATTGTGAGAACATATTTAGAAGATATGTGATGTTACCTTCA
GGAGAAGTGACAATCCAGGACAGGGGGAACCCCTCTGGACAAATATCCACAACTATGGATAATAACATCTGTAATGTCT
TTTTCCAGGCATTTGAGTTTGCATATCTGAATACTGAATTGGATTCTGATGAATTGAAGGAAAATTGGGATAAGTATGA
CTCACTTATCTATGGAGATGACAGGCTAACCACAACCCCTATTTTATGTGACAATTATGTGGACAGAGTTATTAAAATG
TATGCTGATGTCTTTGGGATGTGGGTCAAGAGAGAGAAAGTAAAAGTTTCAAATGAAATTAATGGATGACCTTTGTG
GCTTTACTGTTCAAGAGTCAAATGGCCTTTTTGTCCCATACCAACTGATACAGATAAATTACTTGCTGGCTTAATAAC
ACCAATAAAGAAATTGCCTGATATTTTGTCACTCTATGGGAAGCTCCTTTGCTACCGCATCCTTGGCCATAACTTGCCT
GATGACCATAAATTTAAAAATTATATCTTGGTCGCCTTGAGGTAGTGGCCAGGCACATCCGTGCTAGTGGTGGGGAAG
AACCCTATTATATCACGGATAGCATGCTGGATAGGCTTTGGAGGGGAGGTCCAAAGCAAAGTCATGGCTGGTAG
```

Figure 5

SEQ ID NO: 5 (ORF1b)

```
KKLEGGPETGAPKPEQLRLGYWRELLKPGEYYLTPPHCPLVGVLPIDRPISDYDEPIDDLLNLLPKCEEKPPYAPSTWG
PEAYRRSFDKFFYRKPTENIREKYPREWKFAMSVLRREFDFLQDSVLIDITSTSKNADSTPAYPKTLWWKTETEYLKER
GYQDYIKELDSIRSGERPDVLWYLFLKKEILKISKIEEEDIRQIVCADPIFSRIGCVFEEHQNQLMKNRTLTRMGQCGW
SPFMGGFHKRIKRLVDKGNDYFIEFDWTRYDGTIPNEVFKAIKDFRFSCLRGDLQTKENRDVYNWYCENIFRRYVMLPS
GEVTIQDRGNPSGQISTTMDNNICNVFFQAFEFAYLNTELDSDELKENWDKYDSLIYGDDRLTTTPILCDNYVDRVIKM
YADVFGMWVKREKVKVSNEINGLTFCGFTVQESNGLFVPIPTDTDKLLAGLITPIKKLPDILSLYGKLLCYRILGHNLP
DDHKFKNYILVALEVVARHIRASGGEEPYYITDSMLDRLWRGGPKQSHGW
```

Figure 6

SEQ ID NO: 6 (ORF2)

ATGGCTGGTAGGCAGCCCCAGCAGGCCCTGCCCAAGGCAGCGGCAAAGCAAATAGCCAAGGAGGTAGTCAAACAGGAGA
AGAAGGAACCAGTGGTGCGTAAAAAGAAACAGTTTTATCCAAATCCAAAGTTTAATAATAGATTTAATAAGAAATTTGT
GAAAAAACAGCTAGATAAAAATTTGAAGAAACAAGGGTTTGAAGGACCAAAAACCTAGATTTGCTGTCACCGTCTCTGCC
ACCATTGGCAAGGTCGGGCCAAATAAAAGTCAGGGACCTGAACTCCAAATATCCACTTTCATGCATCCCAGCTTGATGA
AAGAGCCAAATGATGGCACAAATTTTGGTCCCCTACAGTCAGCAGCTGCACAATGGGGTTTGTGGCGCTTGAAAAATTT
GAGCGTCACGTTTACTCCCCTTGTTGGTCCATCAGCAGTTACCGGGTCTGTTTTCCGCATATCCCTAAACATGGCACAG
TCACCTGGAGCCACGTCATGGGGGGGTCTTGGTGCTAGGAAGCACAAGGATGTTGCTGTGGGAAAGCAGTTCACTTGGA
AGCTACAGAAGGGAGACCTCACAGGCCCCAGGGAAACCTGGTGGCTTACAGACACAAATGAAGAGGGAGCACAAAGTTG
TGGGCCTCTTCTTGAGATCCATGGCCTTGGTGAAACAACTTCTACATACAAGGATGCAGCATGGGCTGGAGACCTCTTC
ATTGTTGAGGTCAGGGGTCGCTGGGAGTTTGCAAATTACAACAGCAAACCTGCATTAGGCATGTTGGAGAGGGTGACTG
AAACTACCAATGCTTCAATTGAAGTAGCTAATGGCAATATGATTATGACAGTTCCACAGAATTCCCAGCTTGCAAGGCA
TATGAGTGAAAGGTTCGAGAGGACCACAAATGCAAGTACTGTTGGTGAAACAATATGGCAGATTGTGGATGAGGGTGCT
GGTTTGGTTGCAAATGTCGCACCACCCCCGTTCACTTGGTTGATCAAAGGGGGATGGTGGTTTGTCAAGAAATTACTAG
GTAGATCAGCAAATACTGATGTCCAATATCTAGTTTATGCATCATTGGCAGACGCCCAAAACAATAGACCTGTAGAGGC
ACAAAATTACACAAAAGTCACACGACAGACAACACTTTCTTCCACGCAAATCAATGCACCTAACACAGGCCCTAACACC
ACTACAGGGTCAATTGGAAATAACAACCAACAGTGGCCGATACCTCCGACAGGGGTGCCGGTTGGTGACTTTTATGTCT
GTGGCAGGATGACAACATTGCATATGGGTGGTCAGTCTGGCATTCAAGCCACGACTCTAGTGAATGGGATGATATATCG
TACAGACCACCCAGAACCATCAACAAGCCCAGTTTCCAATTGGGAATTCACAGTTTTGGAAAAACAACACAATTGTTGGT
GCTGGAATGGGGTGTGTGTGGTTTCAGAAATCCGAAGCACTAGTGTGGACGCTAGATGGCCAGAAGCTGTCAGGATGGA
ACACACTAGATGGTGTTGGTACAACCCAATTGACAGTCGCCTGGAGACAGCATAACAGAACAATTTATGGATGGGCTAA
TGTTGTTGCTTGGAACTCTGAAGAATGGCATACAAATGCAGAACAACCACACCAGCCTATATTGAGGCTGACATATTGG
CTAGTAAAAATTAATGTTTTGTCTGAACCAGAAGATTTTGATGTTGTCCAAAAATCCCCATTAGCTTATTTAGAAGATT
ATACTGCACACAATCAAAATCTGCCATCCAAAAGCTCAACTTCCAAACGTTTCAGAAACGTCGAAGGGGGAGGCACTTT
GCGGGCACAATACTCAACTACTCCCAGGCAAGGGGATTTTGCCGTAATATGGCAGATTGGTAGACATAATTTTGACATG
TCTACCGGTAAGGGTACACCAGTTGAAAGTTTGAGTGATTATGTCATGCCCCAGCAGAAGATGCCCATATTGGTATGT
GGTATCGTGCTTTAACCAGTGTTGGACCAAGATCAGATGTTTTGACCCTTCATTCCACTTGCCAACTGTGGAAAAAGA
TTTGGTTGAGCAGATCATTGATCAAATTCAGCATCGCTACAGATTGACCCCACTGGATTCGGATTCAGACTCCTCTAGT
TCTGATTCCGATTTCGAGCCTGAAGATAGATTTGAGAAGTTAAAAATCTATGAGGGTCTCAGGTCCAGTGGTCTGTCAC
ACCATGTATCTGATGGTGCTGCGATAGCTGTCAAGAAAAAATTGCGCCGAGGCCACGCCGAGTAG

Figure 7

SEQ ID NO: 7 (ORF2)

MAGRQPQQALPKAAAKQIAKEVVKQEKKEPVVRKKKQFYPNPKFNNRFNKKFVKKQLDKNLKKQGFEGPKPRFAVTVSA
TIGKVGPNKSQGPELQISTFMHPSLMKEPNDGTNFGPLQSAAAQWGLWRLKNLSVTFTPLVGPSAVTGSVFRISLNMAQ
SPGATSWGGLGARKHKDVAVGKQFTWKLQKGDLTGPRETWWLTDTNEEGAQSCGPLLEIHGLGETTSTYKDAAWAGDLF
IVEVRGRWEFANYNSKPALGMLERVTETTNASIEVANGNMIMTVPQNSQLARHMSERFERTTNASTVGETIWQIVDEGA
GLVANVAPPPFTWLIKGGWWFVKKLLGRSANTDVQYLVYASLADAQNNRPVEAQNYTKVTRQTTLSSTQINAPNTGPNT
TTGSIGNNNQQWPIPPTGVPVGDFYVCGRMTTLHMGGQSGIQATTLVNGMIYRTDHPEPSTSPVSNWEFTVLENNTIVG
AGMGCVWFQKSEALVWTLDGQKLSGWNTLDGVGTTQLTVAWRQHNRTIYGWANVVAWNSEEWHTNAEQPHQPILRLTYW
LVKINVLSEPEDFDVVQKSPLAYLEDYTTAQSKSATQKLNFQTFQKPEGGGTLRAQYSTTPRQGDFAVIWQIGRHNFDM
STGKGTPVESLSDYVMPQQKDAHIGMWYRALTSVGPRSDVLTLHFHLPTVEKDLVEQIIDQIQHRYRLTPLDSDSDSSS
SDSDFEPEDRFEKLKIYEGLRSSGLSHHVSDGAAIAVKKKLRRGHAE

Figure 8

SEQUENCE LISTING

```
<160> NUMBER OF SEQ ID NOS: 15

<210> SEQ ID NO 1
<211> LENGTH: 6610
<212> TYPE: DNA
<213> ORGANISM: Unknown
<220> FEATURE:
<223> OTHER INFORMATION: Astrovirus VA1

<400> SEQUENCE: 1
ccaaatttgt tggctgtgcc gattggcact ggtgggtcat ggagcgctca tacaagccta      60
gtggcagtag ccactatgat ccctatgata gggtactaca acatggcagt gtcaaagcac     120
ggatacaggg ccttcagctt aataaagtag ctaaaaccaa gcttgaagag atttttttcat   180 gtggtgggcc cttgtgtttt ggctatggtg atgttgagac tactcgtgtc tcaaatggag    240
ttgttgagcc acaaccttta attgttaaga cggtctatgt ctcaggagtg agagagggta    300
atgaatatgt cacttacctt tttaaaccgg gacttaatga ttgggttgag gttgatgcta    360
acatacataa acctactgcc attgttggtg tattgtatca tgagtataac aggcttaaat    420
tagagaatga aagtttgaaa acagagcgct catctttaca attggatata tcaatcctca    480
gacatgagct tgagcgtgca agaccaccaa ctaaaataat taggcctttc agtgttgggt    540
gcattatact gtatggttta ctgattggcc ttttgttttc acacatctca caagctttta    600
ggactggtgt gtgtcttgat ccagatgttg gtgaaacact aaagccacaa acctgtataa    660
actggaagtg ggatggtgga attgaatcag atgagactat tccattttat gataggttta    720
cagcttggta tacaggttta atacaacagt ttaaaagtat gtacaatgac attgtcattg    780
atttagtggt ccaggctttt ggctttgctt acacatggac agctatagca ctgatgatag    840
gcacatatta tatgttgaaa tccaccagcc cagcatatat gctggtgaca ttgatgatgg    900
caactgtgtc aagaatgcag ttatttgcaa tatctgctat acctaaatatg gaggtcactt    960 caatgttttc attgtggtgc tgtatggtat tatactattt taatcaggtt gcagcaatgg   1020
ctgcgtcatt aatgatagca gctatgtgct ctattgtttg cctttttcatg ggtgatgctg   1080 agtatgtgaa agtgataagg ggccatggcg tggttatctt aactgttgtt gtttcccaca   1140
```

-continued

```
tctttagtgt cttgttagtg ccacactggg tcacagtgtt cctaatagtt gcttttagaa    1200
ttgttaggtt aattggagca gttgttggtg agaaaataga agttagaaat tctgagggaa    1260
aagttacaag tgtcatacca acaacaacgt cctggttaaa tcggatttct ggatttgttc    1320
agtccaaatt tacccaaaaa gttagaactg gtataatgtc aacagctaga gtgataccta    1380
atggtgttgt cattgtcgaa tcaaaagaaa gctcaggtac tggcttcagg gttcaaaatt    1440
acatagtcac agccgggcat gttgttggca atgaaacaca aataaaggtt aagtggggag    1500
atgttaatgt ttacacaaaa gttgtttaca tgcatcccac taaggatata gcctatcttg    1560
ccttaccatc agagtatcaa gcactcccaa catacaagtt tgctaagctg attgaggatg    1620
gcaccgttgt cataacatca atggaggact gtggtgtcct tgccgttgcg gttacagaag    1680
gtgttattgt taaagataac ataacatatg ctgttagcac ccgaaacggc atgagtggtt    1740
cacctgttac aaatgttgat ggtagaattg ttggcataca tcaagccaac actggattta    1800
caggcggtgc tgtcattata aagcaagagg atttaccacc ccaaaagaag ccacaaaggg    1860
agatagacct tgagaacaaa attaaagaat tagaggatgc ccttaaaggt cagatgaatc    1920
aaggcctaaa tgaaaatcag atagtcgaat tgattcggct tgctgttggt cgtgagatcg    1980
aaatcttacg gcatgaaatc aatatgaacc aagcaaaagg taaaaataaa aggaagaatc    2040
accacaagag gcgcaggaag ggaaaagttt ggactgaaga ggagtacaaa gacctttgg     2100 aaaagggatt taccagacag caattacggg acatggctga agtgctaaga gaggcagatt    2160
attctgaaga tgatgaaagt gatgagtatg acactggtta tccgcaatgg tcagacccag    2220
aagactctga ggaggttgaa agggaatggt ttgggccaaa gaaaaagata cttgatgagg    2280
ttgaagaagg ttggtccaat actgatttct gggagcagtg tcagaaggtg tggaaggaga    2340
tggagcccat gccggaagaa tctgttaaca ctttaccgtc acacttgagt gataagtatg    2400
gtattacatg ctatgttgtc acaaagagtg atatggaagc cttagcccgt gatttgcagg    2460
aataccaagc caaggttgag gagaagatta aggcaaatgt tgttcgtggt cagtggcttg    2520
agggagtcaa tccaaaaact atcataagtg agttggatga attatggctg aaactgaacc    2580
acttaatgtg gacccatggt atagtccctt tcatacagag gaaaaaaatt aacagaaaga    2640
aacagcaaaa aaacttgaag ggggccccga acaggggcc ccaaaaccag aacaactaag     2700
gcttgggtac tggagagaac tattaaaacc tggtgaatat tatcttaccc ccccacattg    2760
ccccttagtt ggtgttttac caatagatag gcctataagt gattatgatg agccaattga    2820
tgatttacta aatttgttgc caaaatgtga ggaaaagccg ccatacgcac cgtctacatg    2880
gggaccagaa gcgtataggc ggtcatttga taagttcttt tacagaaagc caactgaaaa    2940
tataagagaa aaatatccta gggagtggaa atttgcaatg tcagtgctca gaagagaatt    3000
tgatttccta caggacagtg ttcttattga cataacatcc acttcaaaga atgctgactc    3060
cacacctgct tatccaaaga cattatggtg aaaactgaa acagaatacc ttaaagagcg     3120
gggttaccaa gattacatta aagagttaga ttcaataaga tctggagaga ggcctgatgt    3180
cttatggtat ttatttttaa aaaagagat tttaaagata agtaaaattg aggaagaaga    3240
cattaggcaa attgtttgtg ctgatcccat tttttctaga attggttgtg tatttgaaga    3300
gcaccaaaat caattgatga aaatcgaac cctgacacgt atgggtcaat gtggatggtc    3360
accatttatg ggaggtttcc ataaacgcat aaagcgccta gttgataaag caatgattaa    3420
cttcattgag ttcgactgga cgcgttatga tggtaccatc cctaatgaag tctttaaggc    3480
tattaaggac tttagattct cgtgtcttag gggagacttg caaacaaaag aaaacagaga    3540
```

```
tgtctataat tggtattgtg agaacatatt tagaagatat gtgatgttac cttcaggaga    3600
agtgacaatc caggacaggg ggaacccctc tggacaaata tccacaacta tggataataa    3660
catctgtaat gtcttttcc aggcatttga gtttgcatat ctgaatactg aattggattc     3720
tgatgaattg aaggaaaatt gggataagta tgactcactt atctatggag atgacaggct    3780
aaccacaacc cctattttat gtgacaatta tgtggacaga gttattaaaa tgtatgctga    3840
tgtctttggg atgtgggtca agagagagaa agtaaaagtt tcaaatgaaa ttaatggatt    3900 gacctttgt ggctttactg ttcaagagtc aaatggcctt tttgtcccca taccaactga     3960
tacagataaa ttacttgctg gcttaataac accaataaag aaattgcctg atattttgtc    4020
actctatggg aagctccttt gctaccgcat ccttggccat aacttgcctg atgaccataa    4080
atttaaaaat tatatcttgg tcgccttgga ggtagtggcc aggcacatcc gtgctagtgg    4140
tggggaagaa ccctattata tcacggatag catgctggat aggctttgga ggggaggtcc    4200
aaagcaaagt catggctggt aggcagcccc agcaggccct gcccaaggca gcggcaaagc    4260
aaatagccaa ggaggtagtc aaacaggaga agaaggaacc agtggtgcgt aaaaagaaac    4320
agttttatcc aaatccaaag tttaataata gatttaataa gaaatttgtg aaaaaacagc    4380
tagataaaaa tttgaagaaa caagggtttg aaggaccaaa acctagattt gctgtcaccg    4440
tctctgccac cattggcaag gtcgggccaa ataaaagtca gggacctgaa ctccaaatat    4500
ccactttcat gcatcccagc ttgatgaaag agccaaatga tggcacaaat tttggtcccc    4560
tacagtcagc agctgcacaa tggggtttgt ggcgcttgaa aaatttgagc gtcacgttta    4620
ctccccttgt tggtccatca gcagttaccg ggtctgtttt ccgcatatcc ctaaacatgg    4680
cacagtcacc tggagccacg tcatgggggg gtcttggtgc taggaagcac aaggatgttg    4740
ctgtgggaaa gcagttcact tggaagctac agaagggaga cctcacaggc cccagggaaa    4800
cctggtggct tacagacaca aatgaagagg gagcacaaag ttgtgggcct cttcttgaga    4860
tccatggcct tggtgaaaca acttctacat acaaggatgc agcatgggct ggagacctct    4920
tcattgttga ggtcaggggt cgctgggagt ttgcaaatta caacagcaaa cctgcattag    4980
gcatgttgga gagggtgact gaaactacca atgcttcaat tgaagtagct aatggcaata    5040
tgattatgac agttccacag aattcccagc ttgcaaggca tatgagtgaa aggttcgaga    5100
ggaccacaaa tgcaagtact gttggtgaaa caatatggca gattgtggat gagggtgctg    5160
gtttggttgc aaatgtcgca ccaccccgt tcacttggtt gatcaaaggg ggatggtggt     5220
ttgtcaagaa attactaggt agatcagcaa atactgatgt ccaatatcta gtttatgcat    5280
cattggcaga cgcccaaaac aatagacctg tagaggcaca aaattacaca aaagtcacac    5340
gacagacaac actttcttcc acgcaaatca atgcacctaa cacaggccct aacaccacta    5400
cagggtcaat tggaaataac aaccaacagt ggccgatacc tccgacaggg gtgccggttg    5460
gtgactttta tgtctgtggc aggatgacaa cattgcatat gggtggtcag tctggcattc    5520
aagccacgac tctagtgaat gggatgatat atcgtacaga ccacccagaa ccatcaacaa    5580
gcccagtttc caattgggaa ttcacagttt tggaaaacaa cacaattgtt ggtgctggaa    5640
tggggtgtgt gtggtttcag aaatccgaag cactagtgtg gacgctagat ggccagaagc    5700
tgtcaggatg gaacacacta gatggtgttg gtacaaccca attgacagtc gcctggagac    5760
agcataacag aacaatttat ggatgggcta atgttgttgc ttggaactct gaagaatggc    5820
atacaaatgc agaacaacca caccagccta tattgagggct gacatattgg ctagtaaaaa    5880
ttaatgtttt gtctgaacca gaagattttg atgttgtcca aaaatcccca ttagcttatt    5940
```

```
tagaagatta tactacagca caatcaaaat ctgccatcca aaagctcaac ttccaaacgt    6000
ttcagaaacc tgaaggggga ggcactttgc gggcacaata ctcaactact cccaggcaag    6060
gggattttgc cgtaatatgg cagattggta gacataattt tgacatgtct accggtaagg    6120
gtacaccagt tgaaagtttg agtgattatg tcatgcccca gcagaaagat gcccatattg    6180
gtatgtggta tcgtgcttta accagtgttg gaccaagatc agatgttttg acccttcatt    6240
tccacttgcc aactgtggaa aaagatttgg ttgagcagat cattgatcaa attcagcatc    6300
gctacagatt gaccccactg gattcggatt cagactcctc tagttctgat tccgatttcg    6360
agcctgaaga tagatttgag aagttaaaaa tctatgaggg tctcaggtcc agtggtctgt    6420
cacaccatgt atctgatggt gctgcgatag ctgtcaagaa aaaattgcgc cgaggccacg    6480
ccgagtagga tcgagggtac agcgctaaat tgattactag aggtgttaat caataaatca    6540
ttgatttggt gattgatatg atcaatttga aattgaaatt tccagcaaaa aaaaaaaaaa    6600
aaaaaaaaaa                                                           6610

<210> SEQ ID NO 2
<211> LENGTH: 2661
<212> TYPE: DNA
<213> ORGANISM: Unknown
<220> FEATURE:
<223> OTHER INFORMATION: Astrovirus VA1
<220> FEATURE:
<221> NAME/KEY: misc_feature
<222> LOCATION: (1)...(2661)
<223> OTHER INFORMATION: ORF1a of the AstV-VA1 virus

<400> SEQUENCE: 2
atggagcgct catacaagcc tagtggcagt agccactatg atccctatga tagggtacta      60
caacatggca gtgtcaaagc acggatacag ggccttcagc ttaataaagt agctaaaacc     120
aagcttgaag agattttttc atgtggtggg cccttgtgtt ttggctatgg tgatgttgag     180
actactcgtg tctcaaatgg agttgttgag ccacaacctt taattgttaa gacggtctat     240
gtctcaggag tgagagaggg taatgaatat gtcacttacc tttttaaacc gggacttaat     300
gattgggtta aggttgatgc taacatacat aaacctactg ccattgttgg tgtattgtat     360
catgagtata caggcttaa attagagaat gaaagtttga aaacagagcg ctcatcttta     420
caattggata tatcaatcct cagacatgag cttgagcgtg caagaccacc aactaaaata     480
attaggcctt tcagtgttgg gtgcattata ctgtatggtt tactgattgg ccttttgttt     540
tcacacatct cacaagcttt taggactggt gtgtgtcttg atccagatgt tggtgaaaca     600
ctaaagccac aaacctgtat aaactggaag tgggatggtg aattgaatc agatgagact     660 attccatttt atgataggtt tacagcttgg tatacaggtt aatacaaca gtttaaaagt     720 atgtacaatg acattgtcat tgatttagtg gtccaggctt ttggctttgc ttacacatgg     780
acagctatag cactgatgat aggcacatat tatatgttga atccaccag cccagcatat     840 atgctggtga cattgatgat ggcaactgtg tcaagaatgc agttatttgc aatatctgct     900
atacctaata tggaggtcac ttcaatgttt tcattgtggt gctgtatggt attatactat     960
tttaatcagg ttgcagcaat ggctgcgtca ttaatgatag cagctatgtg ctctattgtt    1020
tgccttttca tgggtgatgc tgagtatgtg aaagtgataa ggggccatgg cgtggttatc    1080
ttaactgttg ttgtttccca catctttagt gtcttgttag tgccacactg ggtcacagtg    1140
ttcctaatag ttgcttttag aattgttagg ttaattggag cagttgttgg tgagaaaata    1200
gaagttagaa attctgaggg aaaagttaca agtgtcatac aacaacaac gtcctggtta    1260
```

-continued

```
aatcggattt ctggatttgt tcagtccaaa tttacccaaa aagttagaac tggtataatg    1320
tcaacagcta gagtgatacc taatggtgtt gtcattgtcg aatcaaaaga aagctcaggt    1380
actggcttca gggttcaaaa ttacatagtc acagccgggc atgttgttgg caatgaaaca    1440
caaataaagg ttaagtgggg agatgttaat gtttacacaa aagttgttta catgcatccc    1500
actaaggata tagcctatct tgccttacca tcagagtatc aagcactccc aacatacaag    1560
tttgctaagc tgattgagga tggcaccgtt gtcataacat caatggagga ctgtggtgtc    1620
cttgccgttg cggttacaga aggtgttatt gttaaagata acataacata tgctgttagc    1680
acccgaaacg gcatgagtgg ttcacctgtt acaaatgttg atggtagaat tgttggcata    1740
catcaagcca acactggatt tacaggcggt gctgtcatta taaagcaaga ggatttacca    1800
ccccaaaaga agccacaaag ggagatagac cttgagaaca aaattaaaga attagaggat    1860
gcccttaaag gtcagatgaa tcaaggccta aatgaaaatc agatagtcga attgattcgg    1920
cttgctgttg gtcgtgagat cgaaatctta cggcatgaaa tcaatatgaa ccaagcaaaa    1980
ggtaaaaata aaaggaagaa tcaccacaag aggcgcagga agggaaaagt ttggactgaa    2040
gaggagtaca aagacctttt ggaaaaggga tttaccagac agcaattacg ggacatggct    2100
gaagtgctaa gagaggcaga ttattctgaa gatgatgaaa gtgatgagta tgacactggt    2160
tatccgcaat ggtcagaccc agaagactct gaggaggttg aaagggaatg gtttgggcca    2220
aagaaaaaga tacttgatga ggttgaagaa ggttggtcca atactgattt ctgggagcag    2280
tgtcagaagg tgtggaagga gatggagccc atgccggaag aatctgttaa cactttaccg    2340
tcacacttga gtgataagta tggtattaca tgctatgttc tcacaaagag tgatatggaa    2400
gccttagccc gtgatttgca ggaataccaa gccaaggttg aggagaagat taaggcaaat    2460
gttgttcgtg gtcagtggct tgagggagtc aatccaaaaa ctatcataag tgagttggat    2520
gaattatggc tgaaactgaa ccacttaatg tggacccatg gtatagtccc tttcatacag    2580
aggaaaaaaa ttaacagaaa gaaacagcaa aaaaacttga gggggcccc gaaacagggg    2640 ccccaaaacc agaacaacta a                                             2661
```

<210> SEQ ID NO 3
<211> LENGTH: 886
<212> TYPE: PRT
<213> ORGANISM: Unknown
<220> FEATURE:
<223> OTHER INFORMATION: Astrovirus VA1
<220> FEATURE:
<221> NAME/KEY: PEPTIDE
<222> LOCATION: (1)...(886)
<223> OTHER INFORMATION: polypeptide sequence of ORF1a of AstV-VA1 virus

<400> SEQUENCE: 3

Met Glu Arg Ser Tyr Lys Pro Ser Gly Ser Ser His Tyr Asp Pro Tyr
1               5                   10                  15

Asp Arg Val Leu Gln His Gly Ser Val Lys Ala Arg Ile Gln Gly Leu
            20                  25                  30

Gln Leu Asn Lys Val Ala Lys Thr Lys Leu Glu Glu Ile Phe Ser Cys
        35                  40                  45

Gly Gly Pro Leu Cys Phe Gly Tyr Gly Asp Val Glu Thr Thr Arg Val
    50                  55                  60

Ser Asn Gly Val Val Glu Pro Gln Pro Leu Ile Val Lys Thr Val Tyr
65                  70                  75                  80

Val Ser Gly Val Arg Glu Gly Asn Glu Tyr Val Thr Tyr Leu Phe Lys
                85                  90                  95

-continued

```
Pro Gly Leu Asn Asp Trp Val Glu Val Asp Ala Asn Ile His Lys Pro
                100                 105                 110
Thr Ala Ile Val Gly Val Leu Tyr His Glu Tyr Asn Arg Leu Lys Leu
        115                 120                 125
Glu Asn Glu Ser Leu Lys Thr Glu Arg Ser Ser Leu Gln Leu Asp Ile
130                 135                 140
Ser Ile Leu Arg His Glu Leu Glu Arg Ala Arg Pro Pro Thr Lys Ile
145                 150                 155                 160
Ile Arg Pro Phe Ser Val Gly Cys Ile Ile Leu Tyr Gly Leu Leu Ile
                165                 170                 175
Gly Leu Leu Phe Ser His Ile Ser Gln Ala Phe Arg Thr Gly Val Cys
            180                 185                 190
Leu Asp Pro Asp Val Gly Glu Thr Leu Lys Pro Gln Thr Cys Ile Asn
            195                 200                 205
Trp Lys Trp Asp Gly Gly Ile Glu Ser Asp Glu Thr Ile Pro Phe Tyr
210                 215                 220
Asp Arg Phe Thr Ala Trp Tyr Thr Gly Leu Ile Gln Gln Phe Lys Ser
225                 230                 235                 240
Met Tyr Asn Asp Ile Val Ile Asp Leu Val Gln Ala Phe Gly Phe
                245                 250                 255
Ala Tyr Thr Trp Thr Ala Ile Ala Leu Met Ile Gly Thr Tyr Tyr Met
            260                 265                 270
Leu Lys Ser Thr Ser Pro Ala Tyr Met Leu Val Thr Leu Met Met Ala
        275                 280                 285
Thr Val Ser Arg Met Gln Leu Phe Ala Ile Ser Ala Ile Pro Asn Met
290                 295                 300
Glu Val Thr Ser Met Phe Ser Leu Trp Cys Cys Met Val Leu Tyr Tyr
305                 310                 315                 320
Phe Asn Gln Val Ala Ala Met Ala Ala Ser Leu Met Ile Ala Ala Met
                325                 330                 335
Cys Ser Ile Val Cys Leu Phe Met Gly Asp Ala Glu Tyr Val Lys Val
            340                 345                 350
Ile Arg Gly His Gly Val Ile Leu Thr Val Val Ser His Ile
            355                 360                 365
Phe Ser Val Leu Leu Val Pro His Trp Val Thr Val Phe Leu Ile Val
        370                 375                 380
Ala Phe Arg Ile Val Arg Leu Ile Gly Ala Val Val Gly Glu Lys Ile
385                 390                 395                 400
Glu Val Arg Asn Ser Glu Gly Lys Val Thr Ser Val Ile Pro Thr Thr
                405                 410                 415
Thr Ser Trp Leu Asn Arg Ile Ser Gly Phe Val Gln Ser Lys Phe Thr
            420                 425                 430
Gln Lys Val Arg Thr Gly Ile Met Ser Thr Ala Arg Val Ile Pro Asn
        435                 440                 445
Gly Val Val Ile Val Glu Ser Lys Glu Ser Ser Gly Thr Gly Phe Arg
        450                 455                 460
Val Gln Asn Tyr Ile Val Thr Ala Gly His Val Val Gly Asn Glu Thr
465                 470                 475                 480
Gln Ile Lys Val Lys Trp Gly Asp Val Asn Val Tyr Thr Lys Val Val
                485                 490                 495
Tyr Met His Pro Thr Lys Asp Ile Ala Tyr Leu Ala Leu Pro Ser Glu
            500                 505                 510
Tyr Gln Ala Leu Pro Thr Tyr Lys Phe Ala Lys Leu Ile Glu Asp Gly
        515                 520                 525
```

Thr Val Val Ile Thr Ser Met Glu Asp Cys Gly Val Leu Ala Val Ala
    530                 535                 540

Val Thr Glu Gly Val Ile Val Lys Asp Asn Ile Thr Tyr Ala Val Ser
545                 550                 555                 560

Thr Arg Asn Gly Met Ser Gly Ser Pro Val Thr Asn Val Asp Gly Arg
                565                 570                 575

Ile Val Gly Ile His Gln Ala Asn Thr Gly Phe Thr Gly Gly Ala Val
                580                 585                 590

Ile Ile Lys Gln Glu Asp Leu Pro Pro Gln Lys Lys Pro Gln Arg Glu
            595                 600                 605

Ile Asp Leu Glu Asn Lys Ile Lys Glu Leu Glu Asp Ala Leu Lys Gly
        610                 615                 620

Gln Met Asn Gln Gly Leu Asn Glu Asn Gln Ile Val Glu Leu Ile Arg
625                 630                 635                 640

Leu Ala Val Gly Arg Glu Ile Glu Ile Leu Arg His Glu Ile Asn Met
                645                 650                 655

Asn Gln Ala Lys Gly Lys Asn Lys Arg Lys Asn His His Lys Arg Arg
                660                 665                 670

Arg Lys Gly Lys Val Trp Thr Glu Glu Tyr Lys Asp Leu Leu Glu
            675                 680                 685

Lys Gly Phe Thr Arg Gln Gln Leu Arg Asp Met Ala Glu Val Leu Arg
690                 695                 700

Glu Ala Asp Tyr Ser Glu Asp Glu Ser Asp Glu Tyr Asp Thr Gly
705                 710                 715                 720

Tyr Pro Gln Trp Ser Asp Pro Glu Asp Ser Glu Val Glu Arg Glu
                725                 730                 735

Trp Phe Gly Pro Lys Lys Ile Leu Asp Glu Val Glu Glu Gly Trp
                740                 745                 750

Ser Asn Thr Asp Phe Trp Glu Gln Cys Gln Lys Val Trp Lys Glu Met
                755                 760                 765

Glu Pro Met Pro Glu Glu Ser Val Asn Thr Leu Pro Ser His Leu Ser
770                 775                 780

Asp Lys Tyr Gly Ile Thr Cys Tyr Val Val Thr Lys Ser Asp Met Glu
785                 790                 795                 800

Ala Leu Ala Arg Asp Leu Gln Glu Tyr Gln Ala Lys Val Glu Glu Lys
                805                 810                 815

Ile Lys Ala Asn Val Val Arg Gly Gln Trp Leu Glu Gly Val Asn Pro
            820                 825                 830

Lys Thr Ile Ile Ser Glu Leu Asp Glu Leu Trp Leu Lys Leu Asn His
        835                 840                 845

Leu Met Trp Thr His Gly Ile Val Pro Phe Ile Gln Arg Lys Lys Ile
    850                 855                 860

Asn Arg Lys Lys Gln Gln Lys Asn Leu Lys Gly Ala Pro Lys Gln Gly
865                 870                 875                 880

Pro Gln Asn Gln Asn Asn
                885

<210> SEQ ID NO 4
<211> LENGTH: 1575
<212> TYPE: DNA
<213> ORGANISM: Unknown
<220> FEATURE:
<223> OTHER INFORMATION: Astrovirus VA1
<220> FEATURE:
<221> NAME/KEY: misc_feature
<222> LOCATION: (1)...(1575)

-continued

<223> OTHER INFORMATION: nucleotide sequence of ORF1b of ASTV-VA1 virus

<400> SEQUENCE: 4

| | | | | | |
|---|---|---|---|---|---|
| aaaaaacttg | aagggggccc | cgaaacaggg | gccccaaaac | cagaacaact | aaggcttggg | 60 |
| tactggagag | aactattaaa | acctggtgaa | tattatctta | cccccccaca | ttgcccctta | 120 |
| gttggtgttt | taccaataga | taggcctata | agtgattatg | atgagccaat | tgatgattta | 180 |
| ctaaatttgt | tgccaaaatg | tgaggaaaag | ccgccatacg | caccgtctac | atggggacca | 240 |
| gaagcgtata | ggcggtcatt | tgataagttc | ttttacagaa | agccaactga | aaatataaga | 300 |
| gaaaaatatc | ctagggagtg | gaaatttgca | atgtcagtgc | tcagaagaga | atttgatttc | 360 |
| ctacaggaca | gtgttcttat | tgacataaca | tccacttcaa | agaatgctga | ctccacacct | 420 |
| gcttatccaa | agacattatg | gtggaaaact | gaaacagaat | accttaaaga | gcggggttac | 480 |
| caagattaca | ttaaagagtt | agattcaata | agatctggag | agaggcctga | tgtcttatgg | 540 |
| tatttatttt | taaaaaaaga | gatttttaaag | ataagtaaaa | ttgaggaaga | agacattagg | 600 |
| caaattgttt | gtgctgatcc | catttttttct | agaattggtt | gtgtatttga | agagcaccaa | 660 |
| aatcaattga | tgaaaaatcg | aaccctgaca | cgtatgggtc | aatgtggatg | gtcaccattt | 720 |
| atgggaggtt | tccataaacg | cataaagcgc | ctagttgata | aaggcaatga | ttacttcatt | 780 |
| gagttcgact | ggacgcgtta | tgatggtacc | atccctaatg | aagtctttaa | ggctattaag | 840 |
| gactttagat | tctcgtgtct | taggggagac | ttgcaaacaa | agaaaacag | agatgtctat | 900 |
| aattggtatt | gtgagaacat | atttagaaga | tatgtgatgt | taccttcagg | agaagtgaca | 960 |
| atccaggaca | gggggaaccc | ctctggacaa | atatccacaa | ctatggataa | taacatctgt | 1020 |
| aatgtctttt | tccaggcatt | tgagtttgca | tatctgaata | ctgaattgga | ttctgatgaa | 1080 |
| ttgaaggaaa | attgggataa | gtatgactca | cttatctatg | gagatgacag | gctaaccaca | 1140 |
| accctatt | tatgtgacaa | ttatgtggac | agagttatta | aaatgtatgc | tgatgtcttt | 1200 |
| gggatgtggg | tcaagagaga | gaaagtaaaa | gtttcaaatg | aaattaatgg | attgacctttt | 1260 |
| tgtggcttta | ctgttcaaga | gtcaaatggc | cttttttgtcc | ccataccaac | tgatacagat | 1320 |
| aaattacttg | ctggcttaat | aacaccaata | agaaaattgc | ctgatatttt | gtcactctat | 1380 |
| gggaagctcc | tttgctaccg | catccttggc | cataacttgc | ctgatgacca | taaatttaaa | 1440 |
| aattatatct | tggtcgccctt | ggaggtagtg | gccaggcaca | tccgtgctag | tggtggggaa | 1500 |
| gaaccctatt | atatcacgga | tagcatgctg | gataggcttt | ggaggggagg | tccaaagcaa | 1560 |
| agtcatggct | ggtag | | | | | 1575 |

<210> SEQ ID NO 5
<211> LENGTH: 524
<212> TYPE: PRT
<213> ORGANISM: Unknown
<220> FEATURE:
<223> OTHER INFORMATION: Astrovirus VA1
<220> FEATURE:
<221> NAME/KEY: PEPTIDE
<222> LOCATION: (1)...(524)
<223> OTHER INFORMATION: polypeptide sequence of ORF1b of AstV-VA1 virus

<400> SEQUENCE: 5

Lys Lys Leu Glu Gly Gly Pro Glu Thr Gly Ala Pro Lys Pro Glu Gln
 1               5                  10                  15

Leu Arg Leu Gly Tyr Trp Arg Glu Leu Leu Lys Pro Gly Glu Tyr Tyr
                20                  25                  30

Leu Thr Pro Pro His Cys Pro Leu Val Gly Val Leu Pro Ile Asp Arg
            35                  40                  45

```
Pro Ile Ser Asp Tyr Asp Glu Pro Ile Asp Asp Leu Leu Asn Leu Leu
     50                  55                  60
Pro Lys Cys Glu Glu Lys Pro Pro Tyr Ala Pro Ser Thr Trp Gly Pro
 65                  70                  75                  80
Glu Ala Tyr Arg Arg Ser Phe Asp Lys Phe Phe Tyr Arg Lys Pro Thr
                     85                  90                  95
Glu Asn Ile Arg Glu Lys Tyr Pro Arg Glu Trp Lys Phe Ala Met Ser
                100                 105                 110
Val Leu Arg Arg Glu Phe Asp Phe Leu Gln Asp Ser Val Leu Ile Asp
            115                 120                 125
Ile Thr Ser Thr Ser Lys Asn Ala Asp Ser Thr Pro Ala Tyr Pro Lys
        130                 135                 140
Thr Leu Trp Trp Lys Thr Glu Thr Glu Tyr Leu Lys Glu Arg Gly Tyr
145                 150                 155                 160
Gln Asp Tyr Ile Lys Glu Leu Asp Ser Ile Arg Ser Gly Glu Arg Pro
                165                 170                 175
Asp Val Leu Trp Tyr Leu Phe Leu Lys Lys Glu Ile Leu Lys Ile Ser
            180                 185                 190
Lys Ile Glu Glu Asp Ile Arg Gln Ile Val Cys Ala Asp Pro Ile
        195                 200                 205
Phe Ser Arg Ile Gly Cys Val Phe Glu His Gln Asn Gln Leu Met
    210                 215                 220
Lys Asn Arg Thr Leu Thr Arg Met Gly Gln Cys Gly Trp Ser Pro Phe
225                 230                 235                 240
Met Gly Gly Phe His Lys Arg Ile Lys Arg Leu Val Asp Lys Gly Asn
                245                 250                 255
Asp Tyr Phe Ile Glu Phe Asp Trp Thr Arg Tyr Asp Gly Thr Ile Pro
                260                 265                 270
Asn Glu Val Phe Lys Ala Ile Lys Asp Phe Arg Phe Ser Cys Leu Arg
            275                 280                 285
Gly Asp Leu Gln Thr Lys Glu Asn Arg Asp Val Tyr Asn Trp Tyr Cys
    290                 295                 300
Glu Asn Ile Phe Arg Arg Tyr Val Met Leu Pro Ser Gly Glu Val Thr
305                 310                 315                 320
Ile Gln Asp Arg Gly Asn Pro Ser Gly Gln Ile Ser Thr Thr Met Asp
                325                 330                 335
Asn Asn Ile Cys Asn Val Phe Phe Gln Ala Phe Glu Phe Ala Tyr Leu
            340                 345                 350
Asn Thr Glu Leu Asp Ser Asp Glu Leu Lys Glu Asn Trp Asp Lys Tyr
        355                 360                 365
Asp Ser Leu Ile Tyr Gly Asp Asp Arg Leu Thr Thr Thr Pro Ile Leu
    370                 375                 380
Cys Asp Asn Tyr Val Asp Arg Val Ile Lys Met Tyr Ala Asp Val Phe
385                 390                 395                 400
Gly Met Trp Val Lys Arg Glu Lys Val Lys Val Ser Asn Glu Ile Asn
                405                 410                 415
Gly Leu Thr Phe Cys Gly Phe Thr Val Gln Glu Ser Asn Gly Leu Phe
            420                 425                 430
Val Pro Ile Pro Thr Asp Thr Asp Lys Leu Leu Ala Gly Leu Ile Thr
        435                 440                 445
Pro Ile Lys Lys Leu Pro Asp Ile Leu Ser Leu Tyr Gly Lys Leu Leu
    450                 455                 460
Cys Tyr Arg Ile Leu Gly His Asn Leu Pro Asp Asp His Lys Phe Lys
```

-continued

```
465                 470                 475                 480

Asn Tyr Ile Leu Val Ala Leu Glu Val Val Ala Arg His Ile Arg Ala
                485                 490                 495

Ser Gly Gly Glu Glu Pro Tyr Tyr Ile Thr Asp Ser Met Leu Asp Arg
            500                 505                 510

Leu Trp Arg Gly Gly Pro Lys Gln Ser His Gly Trp
        515                 520

<210> SEQ ID NO 6
<211> LENGTH: 2277
<212> TYPE: DNA
<213> ORGANISM: Unknown
<220> FEATURE:
<223> OTHER INFORMATION: Astrovirus VA1
<220> FEATURE:
<221> NAME/KEY: misc_feature
<222> LOCATION: (1)...(2277)
<223> OTHER INFORMATION: nucleotide sequence of ORF2 of AstV-VA1 virus

<400> SEQUENCE: 6
atggctggta ggcagcccca gcaggccctg cccaaggcag cggcaaagca aatagccaag     60
gaggtagtca aacaggagaa gaaggaacca gtggtgcgta aaaagaaaca gttttatcca    120
aatccaaagt ttaataatag atttaataag aaatttgtga aaaaacagct agataaaaat    180
ttgaagaaac aagggtttga aggaccaaaa cctagatttg ctgtcaccgt ctctgccacc    240
attggcaagg tcgggccaaa taaaagtcag ggacctgaac tccaaatatc cactttcatg    300
catcccagct tgatgaaaga gccaaatgat ggcacaaatt ttggtcccct acagtcagca    360
gctgcacaat ggggtttgtg gcgcttgaaa aatttgagcg tcacgtttac tccccttgtt    420
ggtccatcag cagttaccgg gtctgttttc cgcatatccc taaacatggc acagtcacct    480
ggagccacgt catggggggg tcttggtgct aggaagcaca aggatgttgc tgtgggaaag    540
cagttcactt ggaagctaca gaagggagac ctcacaggcc ccagggaaac ctggtggctt    600
acagacacaa atgaagaggg agcacaaagt tgtgggcctc ttcttgagat ccatggcctt    660
ggtgaaacaa cttctacata caaggatgca gcatgggctg gagacctctt cattgttgag    720
gtcaggggtc gctgggagtt tgcaaattac aacagcaaac ctgcattagg catgttggag    780
agggtgactg aaactaccaa tgcttcaatt gaagtagcta atggcaatat gattatgaca    840
gttccacaga attcccagct tgcaaggcat atgagtgaaa ggttcgagag gaccacaaat    900
gcaagtactg ttggtgaaac aatatggcag attgtggatg agggtgctgg tttggttgca    960
aatgtcgcac cacccccgtt cacttggttg atcaaagggg gatggtggtt tgtcaagaaa   1020
ttactaggta gatcagcaaa tactgatgtc caatatctag tttatgcatc attggcagac   1080
gcccaaaaca atagacctgt agaggcacaa aattacacaa aagtcacacg acagacaaca   1140
ctttcttcca cgcaaatcaa tgcacctaac acaggcccta acaccactac agggtcaatt   1200
ggaaataaca accaacagtg gccgatacct ccgacagggg tgccggttgg tgacttttat   1260
gtctgtggca ggatgacaac attgcatatg ggtggtcagt ctggcattca agccacgact   1320
ctagtgaatg ggatgatata tcgtacagac cacccagaac catcaacaag cccagtttcc   1380
aattgggaat tcacagtttt ggaaaacaac acaattgttg gtgctggaat ggggtgtgtg   1440
tggtttcaga aatccgaagc actagtgtgg acgctagatg gccagaagct gtcaggatgg   1500
aacacactag atggtgttgg tacaacccaa ttgacagtcg cctggagaca gcataacaga   1560
acaatttatg gatgggctaa tgttgttgct tggaactctg aagaatggca tacaaatgca   1620
gaacaaccac accagcctat attgaggctg acatattggc tagtaaaaat taatgttttg   1680
```

-continued

```
tctgaaccag aagattttga tgttgtccaa aaatccccat tagcttattt agaagattat    1740
actacagcac aatcaaaatc tgccatccaa agctcaact  tccaaacgtt tcagaaacct    1800 gaaggggag  gcactttgcg gcacaatac  tcaactactc ccaggcaagg ggattttgcc    1860
gtaatatggc agattggtag acataatttt gacatgtcta ccggtaaggg tacaccagtt    1920
gaaagtttga gtgattatgt catgccccag cagaaagatg cccatattgg tatgtggtat    1980
cgtgctttaa ccagtgttgg accaagatca gatgttttga cccttcattt ccacttgcca    2040
actgtggaaa aagatttggt tgagcagatc attgatcaaa ttcagcatcg ctacagattg    2100
accccactgg attcggattc agactcctct agttctgatt ccgatttcga gcctgaagat    2160
agatttgaga gttaaaaat  ctatgagggt ctcaggtcca gtggtctgtc acaccatgta    2220
tctgatggtg ctgcgatagc tgtcaagaaa aaattgcgcc gaggccacgc cgagtag      2277
```

<210> SEQ ID NO 7
<211> LENGTH: 758
<212> TYPE: PRT
<213> ORGANISM: Unknown
<220> FEATURE:
<223> OTHER INFORMATION: Astrovirus VA1
<220> FEATURE:
<221> NAME/KEY: PEPTIDE
<222> LOCATION: (1)...(758)
<223> OTHER INFORMATION: polypeptide sequence of ORF2 of AstV-VA1 virus

<400> SEQUENCE: 7

```
Met Ala Gly Arg Gln Pro Gln Gln Ala Leu Pro Lys Ala Ala Ala Lys
  1               5                  10                  15

Gln Ile Ala Lys Glu Val Val Lys Gln Glu Lys Lys Glu Pro Val Val
                 20                  25                  30

Arg Lys Lys Lys Gln Phe Tyr Pro Asn Pro Lys Phe Asn Asn Arg Phe
             35                  40                  45

Asn Lys Lys Phe Val Lys Gln Leu Asp Lys Asn Leu Lys Lys Gln
 50                  55                  60

Gly Phe Glu Gly Pro Lys Pro Arg Phe Ala Val Thr Val Ser Ala Thr
 65                  70                  75                  80

Ile Gly Lys Val Gly Pro Asn Lys Ser Gln Gly Pro Glu Leu Gln Ile
                 85                  90                  95

Ser Thr Phe Met His Pro Ser Leu Met Lys Glu Pro Asn Asp Gly Thr
            100                 105                 110

Asn Phe Gly Pro Leu Gln Ser Ala Ala Ala Gln Trp Gly Leu Trp Arg
        115                 120                 125

Leu Lys Asn Leu Ser Val Thr Phe Thr Pro Leu Val Gly Pro Ser Ala
    130                 135                 140

Val Thr Gly Ser Val Phe Arg Ile Ser Leu Asn Met Ala Gln Ser Pro
145                 150                 155                 160

Gly Ala Thr Ser Trp Gly Gly Leu Gly Ala Arg Lys His Lys Asp Val
                165                 170                 175

Ala Val Gly Lys Gln Phe Thr Trp Lys Leu Gln Lys Gly Asp Leu Thr
            180                 185                 190

Gly Pro Arg Glu Thr Trp Trp Leu Thr Asp Thr Asn Glu Glu Gly Ala
        195                 200                 205

Gln Ser Cys Gly Pro Leu Leu Glu Ile His Gly Leu Gly Glu Thr Thr
    210                 215                 220

Ser Thr Tyr Lys Asp Ala Ala Trp Ala Gly Asp Leu Phe Ile Val Glu
225                 230                 235                 240
```

-continued

```
Val Arg Gly Arg Trp Glu Phe Ala Asn Tyr Asn Ser Lys Pro Ala Leu
            245                 250                 255

Gly Met Leu Glu Arg Val Thr Glu Thr Thr Asn Ala Ser Ile Glu Val
        260                 265                 270

Ala Asn Gly Asn Met Ile Met Thr Val Pro Gln Asn Ser Gln Leu Ala
    275                 280                 285

Arg His Met Ser Glu Arg Phe Glu Arg Thr Thr Asn Ala Ser Thr Val
290                 295                 300

Gly Glu Thr Ile Trp Gln Ile Val Asp Glu Gly Ala Gly Leu Val Ala
305                 310                 315                 320

Asn Val Ala Pro Pro Phe Thr Trp Leu Ile Lys Gly Gly Trp Trp
                325                 330                 335

Phe Val Lys Lys Leu Leu Gly Arg Ser Ala Asn Thr Asp Val Gln Tyr
            340                 345                 350

Leu Val Tyr Ala Ser Leu Ala Asp Ala Gln Asn Asn Arg Pro Val Glu
        355                 360                 365

Ala Gln Asn Tyr Thr Lys Val Thr Arg Gln Thr Thr Leu Ser Ser Thr
    370                 375                 380

Gln Ile Asn Ala Pro Asn Thr Gly Pro Asn Thr Thr Gly Ser Ile
385                 390                 395                 400

Gly Asn Asn Asn Gln Gln Trp Pro Ile Pro Pro Thr Gly Val Pro Val
                405                 410                 415

Gly Asp Phe Tyr Val Cys Gly Arg Met Thr Thr Leu His Met Gly Gly
            420                 425                 430

Gln Ser Gly Ile Gln Ala Thr Thr Leu Val Asn Gly Met Ile Tyr Arg
        435                 440                 445

Thr Asp His Pro Glu Pro Ser Thr Ser Pro Val Ser Asn Trp Glu Phe
    450                 455                 460

Thr Val Leu Glu Asn Asn Thr Ile Val Gly Ala Gly Met Gly Cys Val
465                 470                 475                 480

Trp Phe Gln Lys Ser Glu Ala Leu Val Trp Thr Leu Asp Gly Gln Lys
                485                 490                 495

Leu Ser Gly Trp Asn Thr Leu Asp Gly Val Gly Thr Thr Gln Leu Thr
            500                 505                 510

Val Ala Trp Arg Gln His Asn Arg Thr Ile Tyr Gly Trp Ala Asn Val
        515                 520                 525

Val Ala Trp Asn Ser Glu Glu Trp His Thr Asn Ala Glu Gln Pro His
    530                 535                 540

Gln Pro Ile Leu Arg Leu Thr Tyr Trp Leu Val Lys Ile Asn Val Leu
545                 550                 555                 560

Ser Glu Pro Glu Asp Phe Asp Val Val Gln Lys Ser Pro Leu Ala Tyr
                565                 570                 575

Leu Glu Asp Tyr Thr Thr Ala Gln Ser Lys Ser Ala Ile Gln Lys Leu
            580                 585                 590

Asn Phe Gln Thr Phe Gln Lys Pro Glu Gly Gly Thr Leu Arg Ala
        595                 600                 605

Gln Tyr Ser Thr Thr Pro Arg Gln Gly Asp Phe Ala Val Ile Trp Gln
    610                 615                 620

Ile Gly Arg His Asn Phe Asp Met Ser Thr Gly Lys Gly Thr Pro Val
625                 630                 635                 640

Glu Ser Leu Ser Asp Tyr Val Met Pro Gln Gln Lys Asp Ala His Ile
                645                 650                 655

Gly Met Trp Tyr Arg Ala Leu Thr Ser Val Gly Pro Arg Ser Asp Val
            660                 665                 670
```

```
Leu Thr Leu His Phe His Leu Pro Thr Val Glu Lys Asp Leu Val Glu
        675                 680                 685

Gln Ile Ile Asp Gln Ile Gln His Arg Tyr Arg Leu Thr Pro Leu Asp
        690                 695                 700

Ser Asp Ser Asp Ser Ser Ser Asp Ser Asp Phe Glu Pro Glu Asp
705                 710                 715                 720

Arg Phe Glu Lys Leu Lys Ile Tyr Glu Gly Leu Arg Ser Ser Gly Leu
                725                 730                 735

Ser His His Val Ser Asp Gly Ala Ala Ile Ala Val Lys Lys Lys Leu
        740                 745                 750

Arg Arg Gly His Ala Glu
        755
```

<210> SEQ ID NO 8
<211> LENGTH: 19
<212> TYPE: DNA
<213> ORGANISM: Artificial Sequence
<220> FEATURE:
<223> OTHER INFORMATION: forward primer

<400> SEQUENCE: 8
aggggtcgct gggagtttg                                              19

<210> SEQ ID NO 9
<211> LENGTH: 22
<212> TYPE: DNA
<213> ORGANISM: Artificial Sequence
<220> FEATURE:
<223> OTHER INFORMATION: reverse primer

<400> SEQUENCE: 9
gtctattgtt ttgggcgtct gc                                          22

<210> SEQ ID NO 10
<211> LENGTH: 19
<212> TYPE: DNA
<213> ORGANISM: Artificial Sequence
<220> FEATURE:
<223> OTHER INFORMATION: forward primer

<400> SEQUENCE: 10
aggggtcgct gggagtttg                                              19

<210> SEQ ID NO 11
<211> LENGTH: 17
<212> TYPE: DNA
<213> ORGANISM: Artificial Sequence
<220> FEATURE:
<223> OTHER INFORMATION: reverse primer

<400> SEQUENCE: 11
cgggggtggt gcgacat                                                17

<210> SEQ ID NO 12
<211> LENGTH: 33
<212> TYPE: RNA
<213> ORGANISM: Unknown
<220> FEATURE:
<223> OTHER INFORMATION: astrovirus
<220> FEATURE:
<221> NAME/KEY: misc_feature
<222> LOCATION: (1)...(33)
<223> OTHER INFORMATION: promoter for subgenomic RNA synthesis in all
      previously known astroviruses
<220> FEATURE:

-continued

```
<221> NAME/KEY: misc_feature
<222> LOCATION: (1)...(33)
<223> OTHER INFORMATION: n = a, c, g, or u
<220> FEATURE:
<221> NAME/KEY: misc_feature
<222> LOCATION: (21)...(28)
<223> OTHER INFORMATION: n = a, c, g, or u and up to 3 may be absent

<400> SEQUENCE: 12
auuuggagng gnggaccnaa nnnnnnnnau gnc                                  33

<210> SEQ ID NO 13
<211> LENGTH: 26
<212> TYPE: DNA
<213> ORGANISM: Artificial Sequence
<220> FEATURE:
<223> OTHER INFORMATION: forward primer

<400> SEQUENCE: 13
tatccatagt tgtggatatt tgtcca                                          26

<210> SEQ ID NO 14
<211> LENGTH: 22
<212> TYPE: DNA
<213> ORGANISM: Artificial Sequence
<220> FEATURE:
<223> OTHER INFORMATION: reverse primer

<400> SEQUENCE: 14
tgtcttaggg gagacttgca aa                                              22

<210> SEQ ID NO 15
<211> LENGTH: 26
<212> TYPE: DNA
<213> ORGANISM: Artificial Sequence
<220> FEATURE:
<223> OTHER INFORMATION: probe

<400> SEQUENCE: 15
ttccccctgt cctggattgt cacttc                                          26
```

IDENTIFICATION OF ASTROVIRUS VA1 ASSOCIATED WITH GASTROENTERITIS IN HUMANS

CROSS-REFERENCE TO RELATED APPLICATION

This application claims benefit of U.S. Ser. No. 61/182,008 filed 28 May 2009. The contents of this document are incorporated herein by reference.

STATEMENT OF RIGHTS TO INVENTIONS MADE UNDER FEDERALLY SPONSORED RESEARCH

This work was supported in part by a grant from the National Institutes of Health to the Midwest Regional Center of Excellence for Biodefense and Emerging Infectious Diseases Research (2 U54 AI057160-06). The U.S. government has certain rights in this invention.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 295002007900Seqlist.txt | Jul. 28, 2010 | 37,002 bytes |

TECHNICAL FIELD

This invention relates to virology and infectious disease. More particularly, the invention relates to a new human astrovirus.

BACKGROUND ART

Astroviruses are known to infect a variety of avian and mammalian species and typically cause diarrhea. Clinical symptoms usually last 2-4 days and consist of watery diarrhea and, less commonly, vomiting, headache, fever, abdominal pains, and anorexia. They are thought to be host specific with little evidence for cross-species transmission. In humans, 8 serotypes of astroviruses have been described (Mendez, E., et al., *Fields Virology*. 5th ed., Knipe, D. M., Howley, P. M., editors, Lippincott Williams & Wilkins, Philadelphia, Pa. (2007) 981-1000. Recently, a novel astrovirus (Astrovirus MLB1) (Finkbeiner, S. R., et al., *Virol J*. (2008) 5:117; Finkbeiner, S. R., et al., *PLoS Pathog* (2008) 4:e1000011) and a novel picornavirus (Cosavirus E1) (Holtz, L. R., et al., *Virol J*. (2008) 5:159) were identified in diarrhea patients by the present inventors.

Human astroviruses have been associated with up to ~10% of sporadic cases of viral diarrhea in children and with 0.5-15% of outbreaks. Significantly, in some reports the etiologies of 12-41% of the outbreaks remain undetermined even after extensive testing. Similarly, on average, approximately 40% of the cases of sporadic diarrhea are unexplained. It is therefore evident that additional infectious agents associated with diarrhea remain undiscovered.

The present invention relates to an additional infectious agent associated with diarrhea which provides a further means to diagnose, prevent and treat this condition. This agent, designated Astrovirus VA1 (AstV-VA1), was identified and sequenced as associated with a gastroenteritis outbreak at a child care center.

Astroviruses are a family of small, single-stranded, positive-sense RNA viruses. Their genomes are organized into three open reading frames denoted ORF's 1a, 1b, and 2, which encode a serine protease, RNA-dependent RNA polymerase (RdRP), and a capsid precursor protein, respectively. At both the 5' and 3' ends, non-translated regions (NTR) flank the 6.1-7.3 kb sized genomes. Two characteristic features of astroviruses are the dependency on a ribosomal frameshift for the translation of ORF1b and the generation of a sub-genomic RNA from which ORF2 is translated.

DISCLOSURE OF THE INVENTION

The invention relates to a novel astrovirus (AstV-VA1), initially detected in fecal samples from an outbreak of acute gastroenteritis in a child care center by two sequence independent genome amplification and sequencing methods, high throughput pyrosequencing and low throughput Sanger sequencing. The identification and presence of the novel astrovirus was confirmed in both sequencing methods.

Thus, in one aspect, the invention is directed to nucleic acids and proteins associated with AstV-VA1 that are useful in the diagnosis, prevention, and in identification and production of methods of treatment of diarrhea caused by this virus. As further explained below, the new virus is distantly related to the known astrovirus agents associated with diarrhea, and even more distantly related from other causative agents associated with this condition.

While treatment of diarrhea is generally directed to simply alleviating the symptoms, more sophisticated methods of prevention and treatment may be desirable. Similarly, while diagnosis of diarrhea as a condition is self-evident, identification of the causative agent may permit control of epidemiology. These aspects of diagnosis and treatment are specific to the causative agent and thus the identification of this new virus opens up these avenues of diagnosis and control.

Nucleic acids associated with the genome of the AstV-VA1 virus and their complements are useful in methods to produce the proteins, and thus one aspect of the invention is recombinant materials for such production. These include recombinant expression systems wherein heterologous control sequences effect expression of a viral protein or a useful portion thereof. Thus, methods for recombinantly producing viral proteins are included in the invention. These proteins or fragments may then be used in several ways. They may be used to produce antibodies which are also included in the scope of the invention. They may also be used in vaccines for immunizing individuals against infection. The proteins may also be used as screening tools to identify small molecules that may be used as therapeutic agents, somewhat analogous to the development of protease inhibitors in controlling HIV.

The antibodies themselves may be used for passive immunization and for detection of the presence of AstV-VA1 in biological samples or in the environment. They also may be used as targeting agents to couple cytotoxic agents (or detection reagents to seek out the virus itself).

In addition to their use as a tool for recombinant production of viral proteins, the nucleic acid of the AstV-VA1 or its complement, or, typically, portions thereof, may be used as probes or primers for detection of the virus. In addition, the nucleic acids may be used to design ribosomes or antisense nucleic acids that inhibit the replication of the virus or production of viral proteins. Small interfering RNA or other methods of gene silencing may also be used.

Methods for detecting AstV-VA1 either at a protein or nucleic acid level are within the scope of the invention, as are methods to reduce the susceptibility of a subject to such infection or to ameliorate the symptoms by prophylactically administering an immunogenic portion of the virus protein or the attenuated virus itself or by generating antibodies intracellularly using nucleic acids isolated from the invention antibodies.

Methods of identifying therapeutics and designing them are also included.

BRIEF DESCRIPTION OF THE DRAWINGS

FIG. 2 shows the sequence of the AstV-VA1 virus genome (SEQ ID NO:1).

FIG. 3 shows the nucleotide sequence of ORF1a of the AstV-VA1 virus (SEQ ID NO:2).

FIG. 4 shows the polypeptide sequence of ORF1a of the AstV-VA1 virus (SEQ ID NO:3).

FIG. 5 shows the nucleotide sequence of ORF1b of the AstV-VA1 virus (SEQ ID NO:4).

FIG. 6 shows the polypeptide sequence of ORF1b of the AstV-VA1 virus (SEQ ID NO:5).

FIG. 7 shows the nucleotide sequence of ORF2 of the AstV-VA1 virus (SEQ ID NO:6).

FIG. 8 shows the polypeptide sequence of ORF2 of the AstV-VA1 virus (SEQ ID NO:7).

MODES OF CARRYING OUT THE INVENTION

Figure 1:
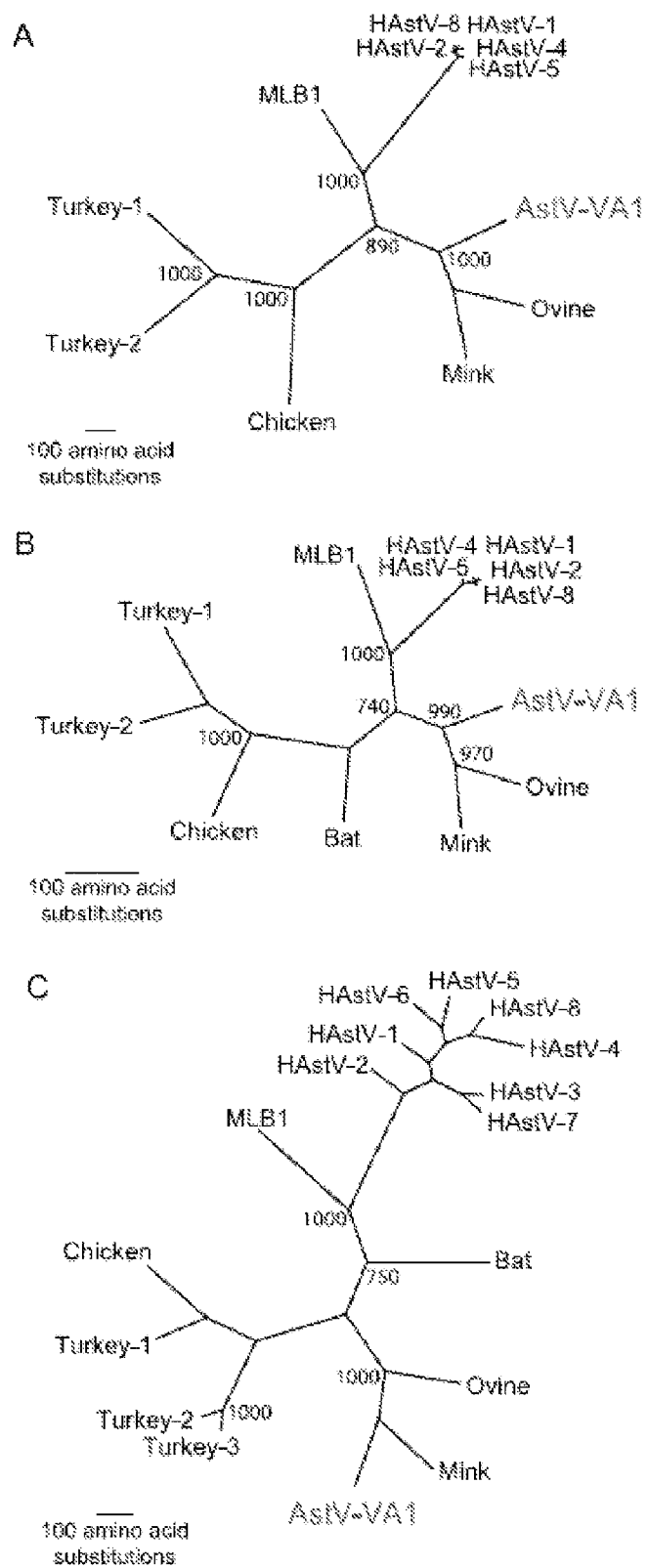
FIGS. 1A-1C illustrate the phylogenetic analysis of AstV-VA1 Virus. Amino acid based phylogenetic trees were generated using PAUP with 1000 bootstrap replicates. Significant bootstrap values are shown. A) ORF1a serine protease; B) ORF1b polymerase; C) ORF2 capsid precursor.

The isolation of AstV-VA1 permits identification and/or preparation of a therapeutic target, an immunogenic agent, a diagnostic agent, or a therapeutic agent previously unavailable to assess and counteract the infectious agents associated with cases of diarrhea that have not been previously characterized. Although AstV-VA1 is in the family of astroviruses known to be associated with the symptoms of diarrhea, as shown in FIGS. 1A-1C this virus is relatively distantly related to the previously known astroviruses at the protein level. Thus, FIG. 1A shows that the serine protease encoded by ORF1a contains hundreds of amino acid substitutions as compared to the previous family of eight human AstV's and even as compared to MLB1. Similarly, the polymerase as shown in FIG. 1B contains hundreds of such substitutions and the capsid protein, as shown in FIG. 1C, contains thousands of such substitutions. It is apparent that antibodies that would successfully detect the known astroviruses would not necessarily be crossreactive with the antibodies that would successfully detect AstV-VA1, nor would nucleic acid probes directed against these prior art viruses be successful in detecting the presence of AstV-VA1. Importantly, immunological compositions which would enhance the resistance of an individual to AstV-VA1 are made available as administering immunogenic portions of the capsid protein of the prior art viruses would not successfully result in such enhancement of the infective agent is AstV-VA1. In addition, antibodies detected in a subject that are immunoreactive with the prior art viruses or their proteins would not offer the opportunity to diagnose infection with AstV-VA1.

Further, the availability of the protease and polymerase of AstV-VA1 permits these proteins to be used to screen for inhibitors of the activity of these proteins which would be useful as therapeutics once the subject is infected. The availability of the nucleic acid of this virus also permits the design of ribozymes and antisense inhibitors of expression. Since the AstV-VA1 is only distantly related to other known astroviruses, and indeed other agents that cause diarrhea in humans, its materials are vital to complete the fabric of diagnostics and vaccines to detect the agent causing this condition as well as immunogenic compositions for its prevention.

Diagnosis of diarrhea per se is, of course, not problematic, but determination of the infectious agent associated with it is important since this permits the epidemiology of an infection to be traced. Thus, an outbreak of diarrhea may, by tracking the causative agent, be traced to a particular source such as a well or food manufacturing plant. Detection of the causative agent is significant in controlling outbreaks of this condition.

The complete nucleotide sequence of AstV-VA1 is shown in FIG. 2. The invention includes useful portions of this sequence and complements thereto. It further includes nucleic acid molecules that hybridize under stringent conditions to SEQ ID NO:1 or its complement or to a significant portion thereof, comprising at least 100 nucleotides, preferably 200 or 300 nucleotides. The term "under stringent conditions" refers to hybridization and washing conditions under which nucleotide sequences having at least 80%, at least 85%, at least 90%, at least 95% or at least 98% identity to each other remain hybridized to each other. In one example, stringent hybridization conditions are hybridization in 6× sodium chloride/sodium citrate (SSC), 0.5% SDS at about 68° C. followed by one or more washes (e.g., about 5 to 30 min each) in 2×SSC, 0.5% SDS at room temperature. In another example, stringent hybridization conditions are hybridization in 6×SSC at about 45° C. followed by one or more washes (e.g., about 5 to 30 min each) in 0.1×SSC, 0.1% SDS at about 45-65° C.

The nucleic acid molecules may be analogous to those occurring in nature, or may have modified linkages such as thioester or phosphoramidate linkages or may be peptide nucleic acids or nucleic acids with other modified backbones so long as the binding specificity of the sequence of bases is retained.

The invention further includes the proteins encoded by the open reading frames of AstV-VA1 or homologs thereof comprising at least 80%, or 85% or 90% or 95% or 98% identity to these sequences. The proteins or polypeptides may also include characteristic immunogenic portions of these sequences and their homologs as well as means to produce them.

By a "characteristic immunogenic portion" is meant a significant portion of the peptide which will elicit antibodies that are specifically reactive with the protein, as opposed to other proteins likely to be present in the same context, such as the proteins encoded by the genomes of other astroviruses or other viruses that cause diarrhea. Thus, the portion will be selected from regions of diversity in the amino acid sequences of the AstV-VA1 protein as compared to other proteins associated with viruses causing diarrhea.

As used herein, "peptide", "protein", and "polypeptide" are used interchangeably without regard to the length of the amino acid chain.

The polypeptides of the invention are useful for the generation of antibodies directed against them or directed against the virus. For use as a vaccine, compositions comprising a polypeptide of SEQ ID NO:7 or a characteristic immunogenic portion thereof are preferred, as these represent the capsid proteins that are exposed on the virus. Attenuated virus vaccines comprising the AstV-VA1 virus itself may also be employed. "Attenuated" virus includes killed or inactivated virus, as well as virus that is merely weakened.

Chimeric AstV-VA1 viruses are also part of the invention. These are recombinant AstV-VA1 viruses which further comprise a heterologous nucleotide sequence. The genome of a chimeric virus contains a nucleotide sequence heterologous to the AstV-VA1 genome.

As used here, "heterologous" refers to a portion of a nucleic acid or a protein that is not natively found coupled to the nucleic acid or protein referred to. Thus, for example control sequences that are heterologous to a coding sequence are those which are not found bound to said coding sequence in nature.

Thus, the invention includes expression systems where heterologous control sequences are coupled operably to sequences encoding the proteins encoded by AstV-VA1 virus or portions thereof. Such expression systems may be included in vectors and transfected into suitable host cells for production of the proteins. Cell types include prokaryotic cells, insect cells, mammalian cells, yeast cells, plant cells and the like.

Primers and probes useful for the amplification and detection of the human astrovirus AstV-VA1 are also included in the invention, as well as methods to detect AstV-VA1 virus employing them. Probes typically contain AstV-VA1 virus (SEQ ID NO:1), sequences substantially identical thereto, or their complements including portions comprising at least 20, 25, 30, 35, 40, 50, 75, 100, 150, 200, 300, 400, or 500 consecutive bases. In one embodiment, a primer or probe comprises an oligonucleotide comprising at least about 20 to 50 consecutive bases of the sequence.

Any suitable method for detecting the presence of AstV-VA1 may be employed but methods that can be adapted to detect the presence of AstV-VA1 virus are well known in the art. For detection of nucleic acids associated with the virus, typically a sample or nucleic acids isolated from the sample are contacted with a probe which can be detected in a variety of ways such as fluorescent or radioactive labels. Alternatively, the nucleic acids in the sample may be first amplified and then identified typically using suitable probes. The presence of viral proteins in the sample can be detected by a wide variety of immunological assays using antibodies of the invention.

The samples for detection may include any tissue or bodily fluid or excretum which is expected to contain an infectious agent. As AstV-VA1 is associated with diarrhea, typically the sample is a fecal sample.

Thus, prior to detection one may amplify the virus or nucleotides of the virus in order to improve sensitivity. Primers useful to amplify the virus bind specifically to AstV-VA1. Exemplary primers include forward primer (5' AGG GGT CGC TGG GAG TTT G 3') (SEQ ID NO:8) and reverse primer (5' GTC TAT TGT TTT GGG CGT CTG C 3') (SEQ ID NO:9) as well as forward primer (5' AGG GGT CGC TGG GAG TTT G 3') (SEQ ID NO:10) and reverse primer (5' CGG GGG TGG TGC GAC AT 3') (SEQ ID NO:11). These primer pairs may be used in nested PCR. Optionally, real time PCR may be used to detect the samples. See Example 3 for an exemplary method of detecting AstV-VA1 in a sample that may be used in some embodiments.

Amplification reactions can also quantify the amount of nucleic acid in a sample, label the nucleic acid (e.g., to apply it to an array or a blot), or detect the nucleic acid. Amplification methods are well known in the art, and include, e.g., polymerase chain reaction (PCR); ligase chain reaction (LCR); transcription amplification; self-sustained sequence replication; Q-Beta replicase amplification; automated Q-Beta replicase amplification assay; and other RNA polymerase mediated techniques.

Antibodies that specifically bind a polypeptide sequence encoded by ORF1a, ORF1b, and ORF2 or portions thereof are included in the invention. An antibody or an antibody fragment is specific for a polypeptide of the AstV-VA1 virus if it permits one of skill in the art to discern the presence of the virus or a protein or peptide encoded by the virus in a sample, and is not cross-reactive with non-AstV-VA1 viral antigens. For detection antibodies include polyclonal, monoclonal, bi-specific, multi-specific, single chain antibodies, diabodies, nanobodies, single domain antibodies (e.g., camel antibodies), Fab, F(ab')$_2$, Fvs, intrabodies and fragments containing either a $V_L$ or $V_H$ domain or even a complementary determining region (CDR) that specifically binds to a polypeptide of the AstV-VA1 virus disclosed herein. Human, humanized and chimeric forms are also included in the invention as these are most useful for passive immunization. Particularly preferred for this application are neutralizing antibodies that can be identified using culture testing or other means.

Antibodies useful in the detection of AstV-VA1 virus can be labeled with any suitable detectable label and employed in assays such as enzyme linked immunosorbent assays (ELISAs), Western blots, immunoprecipitations and immunofluorescence.

Furthermore, provided herein are immunological compositions comprising the virus or portions thereof and a pharmaceutically acceptable carrier. Thus, some compositions can comprise one or more isolated proteins from the AstV-VA1 virus, live AstV-VA1 virus, attenuated AstV-VA1 virus, or inactivated AstV-VA1 virus.

Methods for detecting the presence or absence of a polypeptide or nucleic acid from the AstV-VA1 virus in a biological sample comprises contacting the sample with a compound or an agent capable of detecting an epitope on a protein or nucleic acid (e.g., mRNA, genomic DNA) of the AstV-VA1 virus such that the presence of AstV-VA1 virus is detected in the sample.

Another aspect provides for methods of detecting an antibody, which immunospecifically binds to the AstV-VA1 virus, in a biological sample, for example blood, plasma or serum. In one embodiment, the method comprising contacting the sample with the polypeptides or protein encoded by the nucleotide sequence of AstV-VA1 virus, or a characteristic portion thereof, directly immobilized on a substrate and detecting the virus-bound antibody directly or indirectly by a labeled heterologous anti-isotype antibody.

Kits for detecting the presence of AstV-VA1 virus, or a nucleic acid polypeptide thereof or antibody thereto are included. Kits can also include instructions for use.

For antibody-based kits, the kit can comprise, for example: (1) a first antibody (e.g., attached to a solid support) which binds to a polypeptide or epitope encoded by the AstV-VA1 virus; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence contained within SEQ ID NO:1 or to a sequence within the AstV-VA1 viral genome and/or (2) a pair of primers useful for amplifying a nucleic acid molecule containing an AstV-VA1 viral sequence. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for use.

Yet another aspect provides a method of screening for anti-viral agents useful in reducing the symptoms of AstV-VA1 infections comprising: contacting a cell infected with the human astrovirus AstV-VA1 with a candidate anti-viral agent; assaying the anti-viral agent activity by determining the effect of the agent upon viral titer in the cell, and identifying the agent as an anti-viral agent if it inhibits viral replication, expression, or activity. The methods can be designed to screen for agents in in vitro assays against cell lines infected with the virus, against cells producing an enzyme from a virus or against a purified viral enzyme. Alternatively, the agents may be screened in in vivo assays where the virus is hosted by a mammal.

The availability of the protease and polymerase encoded by AstV-VA1 also offers a screening tool since the inhibitors of the activity of these proteins may be useful in controlling infection.

Identified anti-viral agent can prevent or inhibit the binding of the virus or viral proteins to a host cell under a physiological condition, thereby preventing or inhibiting the infection of the host cell by the virus. Anti-viral agents may prevent or inhibit replication of the viral nucleic acid molecules in the host cell under a physiological condition by interacting with the viral nucleic acid molecules or its transcription mechanisms. The antiviral agent may also inhibit the activity of essential viral proteins as set forth above.

Test viral inhibitory molecules also can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

The following examples are offered to illustrate but not to limit the invention.

Example 1

Genome Sequencing and Analysis

Five fecal specimens (labeled A, B, C, D and E) were collected from a gastroenteritis outbreak at a child care center in Virginia. Symptoms included vomiting and/or diarrhea. The five fecal specimens (A-E) (Table 1) tested negative for enteric parasites, enteric bacteria by standard microscopy and culture, and negative for enteric viruses including rotavirus (RotaClone EIA), norovirus, sapovirus, human astrovirus, and adenovirus gp F by (RT)-PCR.

TABLE 1

Epidemiologic Data of the 5 Specimens from a Child Care Center Outbreak of Acute Gastroenteritis.

| Sample ID | Sex | Age | Onset Date | Sample Date | Symptoms |
|---|---|---|---|---|---|
| A | M | 2 years | Aug. 19, 2008 | Aug. 19, 2008 | Diarrhea, vomiting |
| B | F | 36 years | Aug. 26, 2008 | Aug. 28, 2008 | Diarrhea, vomiting |
| C | M | 6 months | Aug. 25, 2008 | Aug. 25, 2008 | Diarrhea |
| D | M | 19 months | Aug. 5, 2008 | Aug. 26, 2008 | Diarrhea |
| E | Unknown | 20 months | Aug. 5, 2008 | Aug. 27, 2008 | Diarrhea |

Shotgun sequencing of fecal specimens. The fecal specimens were sequenced in parallel at Washington University and at the CDC. At Washington University, the specimens were diluted in PBS at a 1:6 ratio (w/v) and total nucleic acid was extracted from 200 µL of each fecal suspension using the MAGNAPURE™ LC Automated Nucleic Acid Extraction System (Roche). Total nucleic acid was randomly amplified using the Round AB protocol as previously described with the exception that each sample was independently amplified with a different modified primer B containing a unique 6-nucleotide barcode at the 5' end of the primer (Wang, D., et al., *PLoS Biol* (2003) 1:E2). Amplification products from multiple samples were pooled, adaptor-ligated, and sequenced using the Roche GS-FLX™ titanium platform (Roche) at the Washington University Genome Sequencing Center.

Sequences from each sample were identified by the unique barcodes introduced during the Rd B amplification. Primer and barcode sequences were then trimmed off prior to analysis of the sequences. Sequences were clustered using CD-HIT (Li, W., et al., *Bioinformatics* (2006) 22:1658-1659) to reduce redundancy with the requirement that they had to be 98% identical over 98% of their lengths. The longest sequence from each cluster was selected for inclusion in the pool of unique sequences to be analyzed. Unique sequences were filtered for repetitive sequences and compared with the human genome using BLASTn with an e-value cutoff of 1e-10. Sequences without significant similarity to the human genome were then compared to the GenBank nucleic acid database using BLASTn (cutoff: 1e-10) and tBLASTx (cutoff: 1e-5), and remaining sequences without significant hits to sequences in the database were then compared to the NCBI All Viral Genome database located on the World Wide Web using tBLASTx (cutoff: 1e-5) (Altschul, S. F., *Nucleic Acids Res*. (1997) 25:3389-3402). Overlapping sequences with significant sequence identity were assembled into contigs using Newbler (454 Life Sciences) or CAP3 (Huang, X., et al., *Genome Res*. (1999) 9:969-877).

At CDC, 10% fecal suspensions were first clarified by centrifugation at 6,000×g for 10 minutes and the supernatant was then filtered through a 0.22-um filter (ULTRAFREE® MC; Millipore, Bedford, Mass.). Total nucleic acid (TNA) was extracted from 200 µl of the cleared supernatant fluid with the QIAAMP® MINELUTE™ Virus Spin kit (QIAGEN, Valencia, Calif.) according to the manufacturer's instructions. After elution from the column in 50 µl of RNase-free water, TNA was randomly amplified using the Round AB protocol as previously described. The 300-800 bp amplicons were then cloned using the TOPO TA CLONING® kit (Invitrogen, Carlsbad, Calif.) and plasmids were sequenced with a BIGDYE® Terminators v3.1 ready reaction cycle sequencing kit on an ABI PRISM® 3130 automated sequencer (Applied Biosystems, Foster City, Calif.). Sequence analysis and generation of contigs were performed using Sequencher software (Ann Arbor, Mich., USA). Sequence identification was performed through NCBI nucleotide-nucleotide BLASTn similarity searches. In addition, a set of eight overlapping RT-PCR products with an average size of 900 bp which cover the entire genome including the 3' end poly A tail were generated by primer pairs designed from clone sequences as described above, using the SUPERSCRIPT™ III First-Strand Synthesis System for RT-PCR and ACCUPRIME™ High Fidelity Taq DNA polymerase (Invitrogen, Carlsbad, Calif., USA). Both strands of each amplicon were sequenced with a BIGDYE® Terminators v3.1 ready reaction cycle sequencing kit as described above. The 5' end genome sequence was amplified and determined using the 5'/3' RACE Kit (Roche, Mannheim, Germany) following the manufacturer's instructions. The complete genome sequence of AstV-VA1 has been deposited in Genbank and is shown in FIG. 2 as SEQ ID NO:1.

Following high throughput pyrosequencing of RNA and DNA extracted from samples A, B, C and D (average of 12,730 reads per sample), 313 unique high quality sequence reads were found in sample B and 1,017 unique high quality reads were found in sample C most closely related to astroviruses. A 6,376 nucleotide (nt) contig was assembled from the astrovirus-like sequences detected in sample B and 4 contigs totaling 6,026 nucleotides were assembled from sample C. The translated contigs had only limited sequence similarity (37-71% aa identity) to proteins from mink and ovine astroviruses. The five original contigs were then assembled to generate a larger contig of 6,581 nucleotides in length.

Complete genome sequencing and genome analysis. Independently, four of the five fecal samples (stool samples A, B, C and E) were analyzed by Sanger sequencing. Three out of 96 clones from sample B and 69 out of 152 clones from sample C contained sequence signatures that were most closely related to previously known astroviruses by BLASTn similarity searches. Sequencing of 100 clones each from samples A and E yielded no clones with detectable similarity to astroviruses. The sequences of the 69 clones from sample C were assembled into 4 contigs. Primers were then designed to generate a series of eight overlapping RT-PCR amplicons with an average size of ~900 bp that yielded a genomic sequence of 6,537 nt. In order to define the 5' end of the genome, three independent 5'RACE reactions were performed and a total of 23 clones from these reactions were sequenced. All clones extended the genome by 49 nt and yielded the identical 5'end sequence, suggesting that the genome was complete with a total length of 6,586 nt, excluding the poly-A tail. Comparison of the genome sequences generated by the two sequencing methods yielded nearly identical sequences, with the exception of 5 missing nucleotides at the 5' end of the contig generated by pyrosequencing and 3 nucleotide substitution differences. These were resolved by direct PCR sequencing to generate the final, corrected sequence. This virus has been provisionally named Astrovirus VA1 (AstV-VA1).

Open Reading Frame Analysis. The genome of AstV-VA1 had three predicted open reading frames (ORF 1a, 1b, and 2) as well as non-translated regions (NTRs) at both the 5' and 3' ends of the genome. Open reading frames (ORFs) 1a and 2 were predicted by the NCBI ORF Finder located on the World Wide Web. The end of ORF1b was also predicted by NCBI ORF Finder, however the start of ORF1b was predicted based on the location of the heptameric slippery sequence found in other astroviruses. Protein motifs were identified by conserved domain searches using BlastX and Pfam.

Several conserved protein motifs were identified including a serine protease in ORF1a, an RNA dependent RNA polymerase in ORF1b, and capsid protein in ORF 2. ORFs 1a and 2 were predicted by the NCBI ORF Finder program; however the full coding region for ORF1b was not predicted by the program because translation of ORF1b is dependent on a −1 ribosomal frameshift that occurs during translation. This frameshift is thought to be mediated by the presence of a heptameric 'slippery sequence' (AAAAAAAC) near the end of ORF1a, which was also conserved in the AstV-VA1 sequence, suggesting that this new virus follows the same paradigm. The sequence AUUUGGAGNGGNGGAC-CNAAN$_{5-8}$AUGNC (SEQ ID NO:12) located upstream of ORF2, which has been proposed as the promoter for subgenomic RNA synthesis in all previously known astroviruses, is also present in AstV-VA1 with only 2 nt differences. The predicted size for each of the open reading frames is 2,661 nt, 1,575 nt, and 2,277 nt for ORFs 1a, 1b, and 2, respectively. These sizes are similar to the ORF sizes of mink and ovine astroviruses (Table 2).

TABLE 2

Genome Comparison of AstV-VA1 to Other Astroviruses.

| Virus | Genome (bp) | 5' NTR (nt) | ORF1a (nt) | ORF1b (nt) | ORF2 (nt) | 3' NTR (nt) |
|---|---|---|---|---|---|---|
| Chicken AstV-1 | 6,927 | 15 | 3,017 | 1,533 | 2,052 | 305 |
| Turkey AstV-1 | 7,003 | 11 | 3,300 | 1,539 | 2,016 | 130 |
| Turkey AstV-2 | 7,325 | 21 | 3,378 | 1,584 | 2,175 | 196 |
| Mink AstV | 6,610 | 26 | 2,648 | 1,620 | 2,328 | 108 |
| Ovine AstV | 6,440 | 45 | 2,580 | 1,572 | 2,289 | 59 |
| Human AstV-1 | 6,813 | 85 | 2,763 | 1,560 | 2,361 | 80 |
| Human AstV-2 | 6,828 | 82 | 2,763 | 1,560 | 2,392 | 82 |
| Human AstV-4[a] | 6,723 | 84 | 2,763 | 1,548 | 2,316 | 81 |
| Human AstV-5[a] | 6,762 | 83 | 2,763 | 1,548 | 2,352 | 86 |
| Human AstV-8 | 6,759 | 83 | 2,766 | 1,557 | 2,349 | 85 |

TABLE 2-continued

Genome Comparison of AstV-VA1 to Other Astroviruses.

| Virus | Genome (bp) | 5' NTR (nt) | ORF1a (nt) | ORF1b (nt) | ORF2 (nt) | 3' NTR (nt) |
|---|---|---|---|---|---|---|
| AstV-MLB1 | 6,172 | 58 | 2,364 | 1,536 | 2,271 | 58 |
| AstV-VA1 | 6,586 | 38 | 2,661 | 1,575 | 2,277 | 98 |

*a*Numbers were deduced from the full length sequences

The 5' non-translated region (NTR) of AstV-VA1 is 38 nt in length, which is between the lengths of the 5' NTRs of mink astrovirus (26 nt) and ovine astrovirus (45 nt). The 3' NTR is 98 nt in length, which again is intermediate between the length of the NTRs of ovine astrovirus (59 nt) and mink astrovirus (108 nt). The 3' NTR of nearly all astroviruses contains a highly conserved RNA secondary structure called the stem-loop II-like motif (s2m), which has also been identified in several coronaviruses and in equine rhinovirus 2. An alignment of the 150 nt just upstream of the poly-A tail of AstV-VA1 along with the 3' terminal sequences of other astroviruses known to contain the s2m motif indicated that AstV-VA1 contains the highly conserved ~33 nucleotide core of the s2m motif, with 100% identity to other astroviruses in this region. The exact role of this motif is not understood; however its presence in multiple viral families suggests it may play an important role in the replication of these viruses.

Example 2

Phylogenetic Analysis of the Astrovirus VA1 Open Reading Frames

ClustalX (1.83) was used to carry out multiple sequence alignments of the protein sequences associated with all three of the open reading frames of astroviruses for which sequences were available. Maximum parsimony trees were generated using PAUP with 1,000 bootstrap replicates (Swofford, D. L., *PAUP\*. Phylogenetic Analysis Using Parsimony (\*and Other Methods)*, Sunderland, Mass.: Sinauer Associates (1998)). Available nucleotide or protein sequences of the following astroviruses were obtained: Human Astrovirus 1 [GenBank: NC_001943]; Human Astrovirus 2 [GenBank: L13745]; Human Astrovirus 3 [GenBank: AAD17224]; Human Astrovirus 4 [GenBank: DQ070852]; Human Astrovirus 5 [GenBank: DQ028633]; Human Astrovirus 6 [EMBL: CAA86616]; Human Astrovirus 7 [Gen Bank: AAK31913]; Human Astrovirus 8 [GenBank: AF260508]; Turkey Astrovirus 1 [GenBank: Y15936]; Turkey Astrovirus 2 [GenBank: NC_005790]; Turkey Astrovirus 3 [GenBank: AY769616]; Chicken Astrovirus [GenBank: NC_003790]; Ovine Astrovirus [GenBank: NC_002469]; Mink Astrovirus [GenBank: NC_004579], Astrovirus MLB1 [GenBank: NC_011400], and Bat Astrovirus [GenBank: EU847155]. Bioedit was used to determine the percent identity between sequences as determined by pair-wise alignments.

The maximum parsimony trees confirmed that AstV-VA1 was highly divergent from, but most closely related to mink and ovine astrovirus in all three ORFs (FIGS. 1A-1C). Furthermore, the greatest sequence identity between AstV-VA1 and mink and ovine astroviruses is in ORF1b with 61% amino acid identity to mink astrovirus and 62% to ovine astrovirus. The ORF1a (serine protease) coding region was more divergent with 39% and 40% amino acid identity with ovine astrovirus and mink astrovirus, respectively. In ORF2, AstV-VA1 virus shared 41% amino acid identity to mink astrovirus and 42% to ovine astrovirus.

Detailed analysis of the viral DNA sequence and genomic organization confirmed the novelty of AstV-VA1. Complete genome sequencing and phylogenetic analysis demonstrated that AstV-VA1 was highly divergent from all previously described astroviruses including the 8 human astrovirus serotypes and recently described astrovirus MLB1 (AstV-MLB1). AstV-VA1 appears to have diverged from a common ancestor of the mink and ovine astroviruses following their separation from the branch containing human astroviruses 1-8 and astrovirus MLB1. The discovery of AstV-VA1 following the recent identification of AstV-MLB1 clearly demonstrates that a much greater diversity of astroviruses exists in humans than is commonly recognized.

Example 3

Real Time-PCR Screening for AstV-VA1

The samples collected in Example 1 were screened in order to assess the presence of AstV-VA1 in each of the samples. High throughput pyrosequencing yielded many AstV-VA1 sequences in samples B and C, but none were detected in samples A or D. Sample E was not analyzed by pyrosequencing due to technical problems with the sample preparation. Similarly, Sanger sequencing detected AstV-VA1 positive reads in samples B and C, but not in samples A and E (sample D was not initially tested). To determine whether low levels of AstV-VA1 might be present in samples A, D and E, real time RT-PCR and semi-nested RT-PCR assays were developed targeting regions in ORF1b and ORF2, respectively. Using these assays, sample D tested positive and sequencing of the 250 bp amplicon confirmed the presence of AstV-VA1.

Real Time Assay:

The real-time RT-PCR assay was performed using the SUPERSCRIPT™ III One-Step RT-PCR kit (Invitrogen Corp., Carlsbad, Calif.) and the MX4000® system (Stratagene, La Jolla, Calif.). Each 50 μl reaction mixture contained 900 pmol of forward primer (5' TAT CCA TAG TTG TGG ATA TTT GTC CA 3'), 1,000 pmol of reverse primer (5' TGT CTT AGG GGA GAC TTG CAA A 3') and 100 pmol of probe (5' TT CC CCCT GTC CTG GAT TGT CAC TTC 3'), 1× buffer, 6.0 mM MgSO4 (final concentration), 20 units of RNase inhibitor, a 5 pJ aliquot of RNA extracts, and 1 unit of SUPERSCRIPT™ III RT/PLATINUM® TAQ MIX. Water was added to achieve a final volume of 50 μl. The RT-PCR reaction mixture was incubated at 60° C. for 1 minute for denaturing, 50° C. for 30 minutes (for RT), 94° C. for 2 minutes (for hot start), then 40 cycles at 94° C. for 15 seconds; 55° C. for 30 seconds; 72° C. for 30 seconds and a final extension at 72° C. for 7 minutes. Fluorescence measurements were taken and the threshold cycle (CT) value for each sample was calculated by determining the point at which fluorescence exceeded a threshold limit set at the mean plus 10 standard deviations above the baseline.

Semi-Nested RT-PCR Assay:

The first round RT-PCR in the semi-nested assay was performed according to the protocol described previously (Tong, S., et al., *J. Clin. Microbiol.* (2008) 46:2652-2658) using forward primer (5' AGG GGT CGC TGG GAG TTT G 3') and reverse primer (5' GTC TAT TGT TTT GGG CGT CTG C 3'). The 2nd round PCR in the semi-nested assay PCR assay in 50 μl reaction mixture contained 1× buffer (PLATINUM® Taq kit; Invitrogen), 2 mM MgCl2, 200 μM (each) of deoxynucleoside triphosphates, 50 pmol (each) of forward primer (5' AGG GGT CGC TGG GAG TTT G 3') and reverse primer (5' CGG GGG TGG TGC GAC AT 3') 1 U PLATINUM® Taq, one 2-μl aliquot from the first reaction, and water to achieve a final volume of 50 μl. The mixture was first heated to 94° C. for 2 min. The cycling conditions were 40 cycles with the same conditions as for the first amplification: 94° C. for 15 s, primer annealing at 55° C. for 30 s, and 72° C. for 30 s. A final extension was carried out at 72° C. for 7 min. The final semi-nested PCR products were visualized by UV light after electrophoresis on a 2% agarose gel containing 0.5 ug/ml ethidium bromide in 0.5×Tris-borate buffer. Amplicons from the final round of PCR were purified using the QIAQUICK® PCR purification kit (Qiagen, Inc., Valencia, Calif.). Both strands of the amplicons were sequenced with a BIGDYE® Terminators v3.1 ready reaction cycle sequencing kit as described above.

The detection of AstV-VA1 in three out of five samples of this gastroenteritis outbreak suggests a potential association between AstV-VA1 and symptomatic infection. The fact that AstV-VA1 was only detected in sample D by targeted PCR assays and not by either of the mass sequencing methods may be due to the late timing of sample acquisition relative to the onset of symptoms (Table 1). Further studies defining the frequency of detection of AstV-VA1 in additional samples from individuals with and without acute gastroenteritis are needed to define the role of AstV-VA1 in human diarrhea. It is likely that the application of sequence independent amplification and sequencing methods to other outbreaks of gastroenteritis of unknown etiology will identify other novel viruses and expand our ability to determine the cause of diarrheal disease.

The invention claimed is:

1. An isolated nucleic acid molecule comprising a nucleotide sequence at least 95% identical to SEQ ID NO:1, or a complement to the entire said nucleotide sequence.

2. The isolated nucleic acid molecule of claim 1 wherein said nucleotide sequence is at least 98% identical to SEQ ID NO:1, or is a complement to the entire said nucleotide sequence.

3. The isolated nucleic acid molecule of claim 1 wherein said nucleotide sequence is identical to SEQ ID NO:1, or is a complement to the entire said nucleotide sequence.

4. A vector comprising the nucleotide sequence of claim 3 or a complement to the entire said nucleotide sequence.

5. An isolated cell comprising the vector of claim 4.

6. A method to detect the presence of AstV-VA1 in a sample which method comprises contacting the sample with a probe that specifically hybridizes under stringent conditions to the nucleic acid molecule of claim 5, or which method comprises contacting the sample with amplification primers, amplifying nucleic acid in the sample, contacting the amplified nucleic acid with a probe that specifically hybridizes under stringent conditions to the nucleic acid molecule of claim 5, wherein said stringent conditions are 6×SSC at about 45° C. followed by one or more washes of about 5-30 min each in 0.1×SSC, 0.1% SDS at 45-65° C.

* * * * *